(12) United States Patent
Dai et al.

(10) Patent No.: US 11,780,846 B2
(45) Date of Patent: Oct. 10, 2023

(54) COMPOUND, ORGANIC ELECTROLUMINESCENT DEVICE INCLUDING THE SAME AND ELECTRONIC APPARATUS

(71) Applicants: WUHAN TIANMA MICROELECTRONICS CO., LTD., Wuhan (CN); WUHAN TIANMA MICROELECTRONICS CO., LTD. SHANGHAI BRANCH, Shanghai (CN)

(72) Inventors: Wenpeng Dai, Shanghai (CN); Wei Gao, Shanghai (CN); Jinghua Niu, Shanghai (CN); Lei Zhang, Shanghai (CN); Wenjing Xiao, Shanghai (CN)

(73) Assignees: WUHAN TIANMA MICRO-ELECTRONICS CO., LTD., Wuhan (CN); WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 475 days.

(21) Appl. No.: 16/885,139

(22) Filed: May 27, 2020

(65) Prior Publication Data
US 2020/0283448 A1  Sep. 10, 2020

(30) Foreign Application Priority Data
Oct. 30, 2019 (CN) .......................... 201911047167.2

(51) Int. Cl.
| | | |
|---|---|---|
| *H10K 85/40* | (2023.01) | |
| *H10K 85/60* | (2023.01) | |
| *H10K 50/15* | (2023.01) | |
| *H10K 101/30* | (2023.01) | |
| *C07D 487/14* | (2006.01) | |
| *C07D 487/04* | (2006.01) | |
| *C07D 401/14* | (2006.01) | |
| *C07D 491/048* | (2006.01) | |
| *C07D 495/04* | (2006.01) | |
| *C07D 519/00* | (2006.01) | |

(52) U.S. Cl.
CPC ......... *C07D 487/14* (2013.01); *C07D 401/14* (2013.01); *C07D 487/04* (2013.01); *C07D 491/048* (2013.01); *C07D 495/04* (2013.01); *C07D 519/00* (2013.01); *H10K 85/40* (2023.02); *H10K 85/615* (2023.02); *H10K 85/631* (2023.02); *H10K 85/653* (2023.02); *H10K 85/654* (2023.02); *H10K 85/6572* (2023.02); *H10K 85/6574* (2023.02); *H10K 85/6576* (2023.02); *H10K 50/15* (2023.02); *H10K 2101/30* (2023.02)

(58) Field of Classification Search
CPC .. C07D 487/04; C07D 487/14; C07D 401/14; C07D 491/0418; C07D 495/04; C07D 519/00; H10K 85/40; H10K 85/615; H10K 85/631; H10K 85/653; H10K 85/654; H10K 85/6572; H10K 85/6574; H10K 85/6576; H10K 50/15; H10K 101/30
See application file for complete search history.

(56) References Cited

FOREIGN PATENT DOCUMENTS

| | | | |
|---|---|---|---|
| CN | 103108859 | * | 9/2010 |
| CN | 110256415 | A | 9/2019 |
| KR | 20150010094 | A | 1/2015 |
| KR | 20150033329 | A | 4/2015 |
| WO | 2017118237 | A1 | 7/2017 |

* cited by examiner

*Primary Examiner* — Erich A Leeser
(74) *Attorney, Agent, or Firm* — Alston & Bird LLP

(57) ABSTRACT

A compound having a structure represented by Formula I, and an organic electroluminescent device and an electronic apparatus including the same. The compound may be used as a hole transport material of an organic electroluminescent device. The compound provided by the present disclosure has a shallow LUMO, an appropriate HOMO energy level and a high triplet energy level $E_T$, and can effectively improve hole transport ability, and block electron transition and exciton transport; meanwhile, the compound has high electron mobility, and excellent thermal stability and thin film stability. The compound provided by the present disclosure is used as the hole transport material of an organic electroluminescent device, so that the material has good solubility and appropriate mobility and the inter-pixel crosstalk is effectively avoided, which is conducive to improving light emitting efficiency and lifetime of the device.

7 Claims, 1 Drawing Sheet

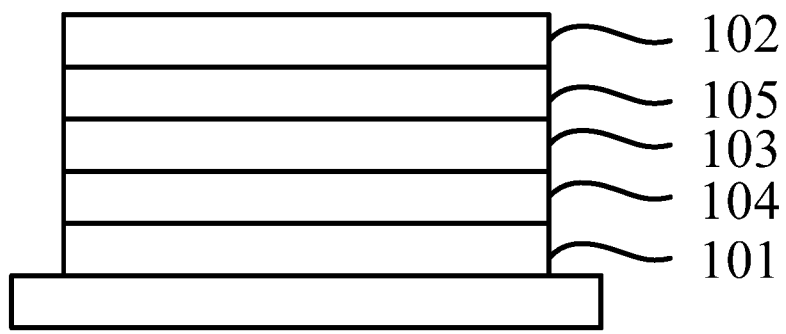

COMPOUND, ORGANIC ELECTROLUMINESCENT DEVICE INCLUDING THE SAME AND ELECTRONIC APPARATUS

CROSS-REFERENCE TO RELATED APPLICATIONS

The present disclosure claims the benefit of the earlier filing date of Chinese Patent Application No. CN201911047167.2, filed on Oct. 30, 2019 to the CNIPA, the contents of which are incorporated by reference herein in its entirety.

TECHNICAL FIELD

The present disclosure is in the field of organic electroluminescent materials and, in particular, relates to a compound, and an organic electroluminescent device and an electronic apparatus including the same.

BACKGROUND

In recent years, organic light emitting diodes (OLEDs) have rapidly become a research hotspot, and have great potential for replacing mainstream liquid crystal displays and becoming a star technology in the display field. The growing demand in the display field has also driven the rapid development of OLED device structures and organic optoelectronic materials. Specifically, compounds and materials with new structures, functional groups and substituents are continuously emerging; meanwhile, the OLED device structures are continuously optimized: an original sandwich structure has gradually developed into a complex structure composed of multiple functional layers. In designs of OLED devices, energy level matching is very important. Take a classic organic electroluminescent device as an example, its laminated structure includes a cathode, an anode and organic films between the cathode and the anode, wherein the organic films include a light emitting layer, an electron transport layer, a hole transport layer, a hole injection layer and an electron injection layer.

At present, small or medium-sized OLED screens such as mobile phones and other consumer products mostly use an R, G and B sub-pixel display method. In order to improve the production yield, some functional layers tend to be designed as common layers, so that fewer fine metal masks (FMM) will be used. The hole transport layer is generally designed as a common layer. A variety of organic compounds that can be used as materials of the hole transport layer have been disclosed in the existing art, and their industrial applications have been achieved. For example, patent EP0721935A1 disclosed a compound that may be used in the hole transport layer of an OLED device. The molecular structure of the compound is

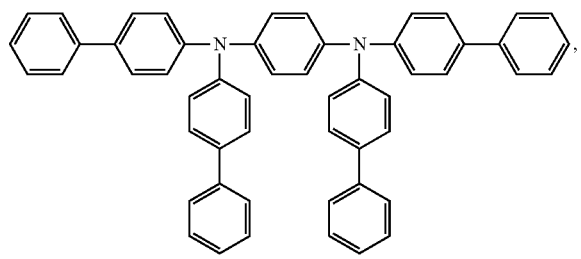 [SMILES: c1ccc(-c2ccc(N(c3ccc(-c4ccccc4)cc3)c3ccc(N(c4ccc(-c5ccccc5)cc4)c4ccc(-c5ccccc5)cc4)cc3)cc2)cc1]

its longitudinal mobility is relatively high, and its lateral mobility is not very high, so that inter-pixel cross-talk will not occur. However, the compound has poor solubility and a low triplet state. CN103108859A disclosed a material for an organic electroluminescent device. A representative compound of such material is

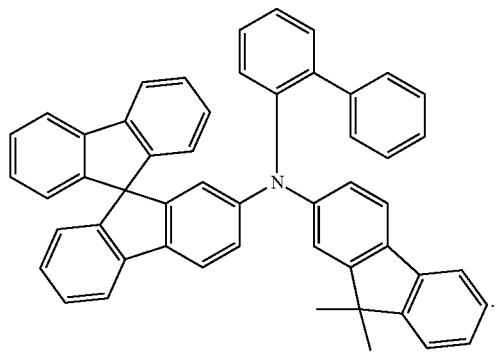 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

The compound has relatively good solubility and high mobility. However, the excessively high mobility of the compound will result in a lateral leakage current to cause cross-talk and affect the light emitting performance of the device.

With the further development of organic electroluminescent devices, it is gradually found that basic functions of the hole transport layer are to increase the hole transport rate in the device and effectively block electrons within the light emitting layer to recombine carriers to a maximum degree, and to decrease the energy barrier during hole injection and increase hole injection efficiency. However, existing hole transport material technology has the following five problems: first, the material has poor solubility, which will result in a poor cleaning effect of evaporation masks during mass production; second, the material has low mobility, which will result in a high overall voltage of the device; third, the material has excessively high mobility, especially excessively high lateral mobility, which results in cross-talk between adjacent pixels; fourth, the lowest unoccupied molecular orbital (LUMO) energy level of the material is too deep to effectively block electrons that might migrate beyond the light emitting layer; fifth, the triplet energy level of the material is too low to effectively achieve hole transport in RGB colors at the same time, so that the number of masks and the process difficulty are increased.

Therefore, it is an urgent problem to be solved in the art to develop a hole transport material with appropriate mobility, solubility and energy level characteristics.

SUMMARY

In an aspect, the present disclosure provides a compound having a structure represented by Formula I:

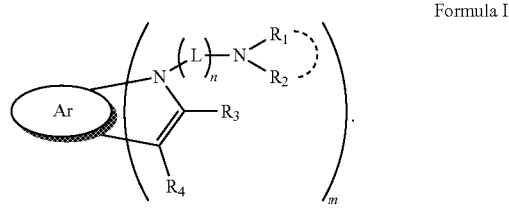

Formula I

In Formula I, Ar is any one selected from the group consisting of substituted or unsubstituted C6 to C18 aryl and substituted or unsubstituted C6 to C18 heteroaryl. CX means the number of carbon atoms contained in the group.

C6 to C18 may be C6, C7, C8, C9, C10, C11, C12, C13, C14, C15, C16, C17 or C18.

In Formula I, L is any one selected from the group consisting of substituted or unsubstituted C1 to C20 linear or branched alkylene, substituted or unsubstituted C6 to C40 arylene and substituted or unsubstituted C3 to C40 heteroarylene.

In Formula I, $R_1$ and $R_2$ are each independently any one selected from the group consisting of substituted or unsubstituted C6 to C40 aryl and substituted or unsubstituted C3 to C40 heteroaryl; and the dashed arc between $R_1$ and $R_2$ indicates that $R_1$ and $R_2$ are not joined to each other or joined to form a ring. The same expression (referring to the dashed arc between $R_1$ and $R_2$) hereinafter has the same meaning.

In Formula I, $R_3$ and $R_4$ are each independently any one selected from the group consisting of C1 to C20 linear or branched alkyl, C3 to C20 cycloalkyl, C6 to C30 arene and C3 to C30 heteroarene.

C1 to C20 may be C2, C4, C6, C8, C10, C13, C15, C17 or C19, etc.

C6 to C40 may be C7, C8, C10, C13, C15, C18, C20, C23, C25, C28, C30, C33, C35, C37 or C39, etc.

C3 to C40 may be C4, C5, C6, C8, C10, C13, C15, C18, C20, C23, C25, C28, C30, C33, C35, C37 or C39, etc.

C3 to C20 may be C4, C5, C6, C8, C10, C13, C15, C17 or C19, etc.

C6 to C30 may be C7, C8, C9, C10, C13, C15, C18, C20, C23, C25, C27 or C29, etc.

C3 to C30 may be C4, C5, C6, C8, C10, C13, C15, C18, C20, C23, C25, C27 or C29, etc.

The expression that "$R_1$ and $R_2$ are not joined to each other or joined to form a ring" means that $R_1$ and $R_2$ may not be joined to each other, or that $R_1$ and $R_2$ are joined to each other via a chemical bond to form a ring. The specific joining and ring forming method is not limited in the present disclosure. The same expression hereinafter has the same meaning.

In formula I, m is an integer from 1 to 3, for example, 1, 2 or 3; and when m is 2 or 3, $R_1$ is the same or different, $R_2$ is the same or different, $R_3$ is the same or different, $R_4$ is the same or different, and L is the same or different.

In formula I, n is 0 or 1.

In another aspect, the present disclosure provides an organic electroluminescent device, including an anode, a cathode and an organic thin film layer disposed between the anode and the cathode, wherein the organic thin film layer includes a hole transport layer, wherein the hole transport layer includes the compound described above.

In another aspect, the present disclosure provides an electronic apparatus, including the organic electroluminescent device described above.

Compared with the existing art, the present disclosure has the following beneficial effects:

The compound provided by the present disclosure includes a special arylpyrrole structure, has a shallow LUMO energy level and an appropriate highest occupied molecular orbital (HOMO) energy level, and can effectively improve hole transport ability and block transitions of electrons. The compound has a high triplet energy level $E_T$ and can effectively block transport of excitons, confine excitons in a light emitting layer, and improve transport of holes. In addition, the compound has high electron mobility, and excellent thermal stability and thin film stability. The compound provided by the present disclosure is used as a hole transport material of an organic electroluminescent device, so that the material has good solubility and appropriate mobility and inter-pixel cross-talk is effectively avoided, which is conducive to improving light emitting efficiency and device lifetime.

BRIEF DESCRIPTION OF DRAWINGS

FIG. 1 is a structural diagram of an organic electroluminescent device provided by the present disclosure, wherein 101 is an anode, 102 is a cathode, 103 is a light emitting layer, 104 is a first organic thin film layer, 105 is a second organic thin film layer, and 104 includes a hole transport layer.

DETAILED DESCRIPTION

The technical solutions of the present disclosure are further described below through specific embodiments. Those skilled in the art should understand that the embodiments are merely used to help understand the present disclosure and should not be regarded as specific limitations to the present disclosure.

In an aspect, the present disclosure provides a compound having a structure represented by Formula I:

Formula I

In Formula I, Ar is any one selected from the group consisting of substituted or unsubstituted C6 to C18 aryl and substituted or unsubstituted C6 to C18 heteroaryl.

C6 to C18 may be C6, C7, C8, C9, C10, C11, C12, C13, C14, C15, C16, C17 or C18.

In Formula I, L is any one selected from the group consisting of substituted or unsubstituted C1 to C20 linear or branched alkylene, substituted or unsubstituted C6 to C40 arylene and substituted or unsubstituted C3 to C40 heteroarylene.

In Formula I, $R_1$ and $R_2$ are each independently any one selected from the group consisting of substituted or unsubstituted C6 to C40 aryl and substituted or unsubstituted C3 to C40 heteroaryl; and the dashed arc between $R_1$ and $R_2$ indicates that $R_1$ and $R_2$ are not joined to each other or joined to form a ring. The same expression (referring to the dashed arc between $R_1$ and $R_2$) hereinafter has the same meaning.

In Formula I, $R_3$ and $R_4$ are each independently any one selected from the group consisting of C1 to C20 linear or branched alkyl, C3 to C20 cycloalkyl, C6 to C30 arene and C3 to C30 heteroarene.

C1 to C20 may be C2, C4, C6, C8, C10, C13, C15, C17 or C19, etc.

C6 to C40 may be C7, C8, C10, C13, C15, C18, C20, C23, C25, C28, C30, C33, C35, C37 or C39, etc.

C3 to C40 may be C4, C5, C6, C8, C10, C13, C15, C18, C20, C23, C25, C28, C30, C33, C35, C37 or C39, etc.

C3 to C20 may be C4, C5, C6, C8, C10, C13, C15, C17 or C19, etc.

C6 to C30 may be C7, C8, C9, C10, C13, C15, C18, C20, C23, C25, C27 or C29, etc.

C3 to C30 may be C4, C5, C6, C8, C10, C13, C15, C18, C20, C23, C25, C27 or C29, etc.

The expression that "$R_1$ and $R_2$ are not joined to each other or joined to form a ring" means that $R_1$ and $R_2$ may not be joined to each other, or that $R_1$ and $R_2$ are joined to each other via a chemical bond to form a ring. The specific joining and ring forming method is not limited in the present disclosure. The same expression hereinafter has the same meaning.

In formula I, m is an integer from 1 to 3, for example, 1, 2 or 3; and when m is 2 or 3, $R_1$ is the same or different, $R_2$ is the same or different, $R_3$ is the same or different, $R_4$ is the same or different, and L is the same or different.

In formula I, n is 0 or 1.

The compound provided by the present disclosure having a arylpyrrole (benzopyrrole) structure has a shallow LUMO energy level and an appropriate HOMO energy level, and can effectively improve the hole transport ability of the material and block transitions of electrons. In addition, the compound has a high triplet energy level and can effectively block transport of excitons, confine excitons in a light emitting layer, and improve device efficiency. The proper distortion and steric hindrance exist between groups in the compound confers the material with good solubility. In addition, the compound has appropriate mobility, and can effectively avoid inter-pixel cross-talk. Therefore, the compound provided by the present disclosure is suitable for use as a hole transport material of an organic electroluminescent device. The compound has excellent hole transport capability, thermal stability and thin film stability, and appropriate mobility, and is conducive to improving light emitting efficiency and the lifetime of the device.

In an embodiment, a substituent in the substituted aryl, substituted heteroaryl, substituted alkylene, substituted arylene or substituted heteroarylene is at least one selected from the group consisting of C1 to C10 (for example, C2, C3, C4, C5, C6, C7, C8 or C9) linear or branched alkyl, C6 to C20 (for example, C7, C9, C10, C12, C14, C15, C17 or C19, etc.) aryl, C3 to C20 (for example, C4, C6, C8, C10, C12, C14, C16 or C18, etc.) heteroaryl and cyano.

In an embodiment, Ar is substituted or unsubstituted C6 to C18 aryl, wherein C6 to C18 may be C6, C7, C8, C9, C10, C11, C12, C13, C14, C15, C16, C17 or C18.

When a substituent is present in the above groups, the substituent is at least one selected from the group consisting of C1 to C10 (for example, C2, C3, C4, C5, C6, C7, C8 or C9) linear or branched alkyl, C6 to C20 (for example, C7, C9, C10, C12, C14, C15, C17 or C19, etc.) aryl, C3 to C20 (for example, C4, C6, C8, C10, C12, C14, C16 or C18, etc.) heteroaryl and cyano.

In an embodiment, Ar is any one selected from the group consisting of substituted or unsubstituted phenyl, substituted or unsubstituted naphthyl, substituted or unsubstituted biphenyl, substituted or unsubstituted anthryl, substituted or unsubstituted phenanthryl and substituted or unsubstituted pyrenyl.

When a substituent is present in the above groups, the substituent is at least one selected from the group consisting of C1 to C10 (for example, C2, C3, C4, C5, C6, C7, C8 or C9) linear or branched alkyl, C6 to C20 (for example, C7, C9, C10, C12, C14, C15, C17 or C19, etc.) aryl, C3 to C20 (for example, C4, C6, C8, C10, C12, C14, C16 or C18, etc.) heteroaryl and cyano.

In an embodiment, m is 2 or 3.

In an embodiment, the compound has a structure represented by any one of Formula II-1 to Formula II-12:

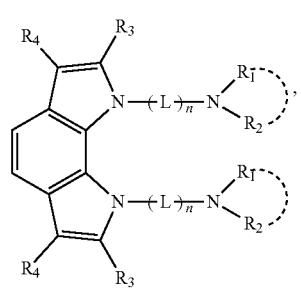

Formula II-1

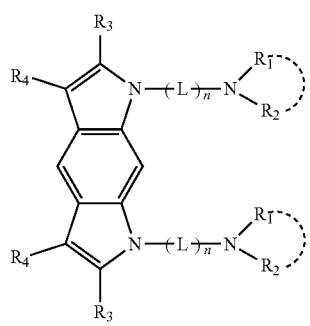

Formula II-2

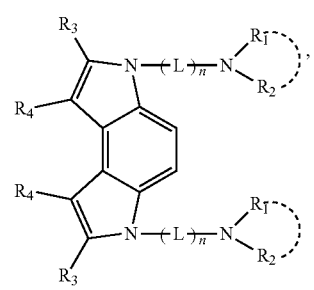

Formula II-3

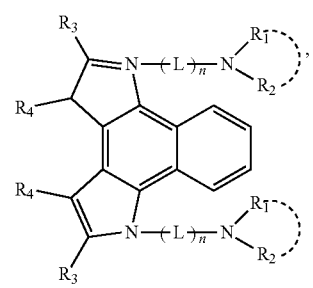

Formula II-4

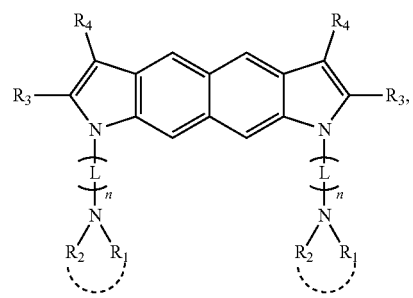

Formula II-5

Formula II-6

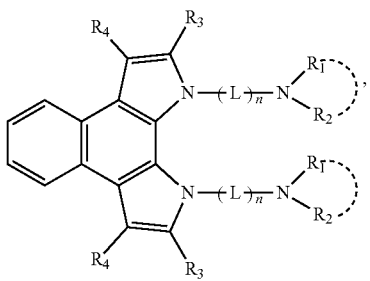

Formula II-7

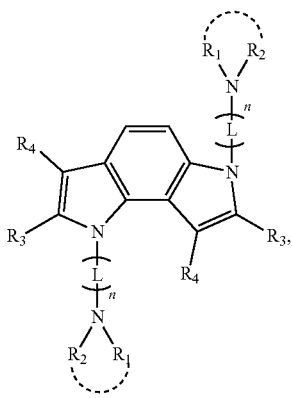

Formula II-8

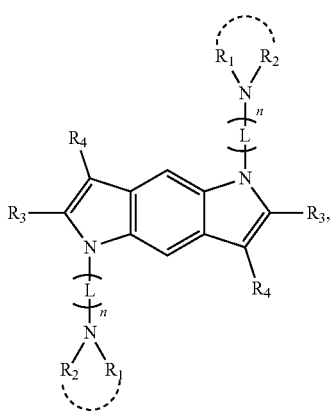

Formula II-9

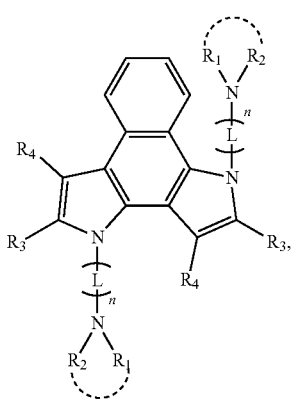

Formula II-10

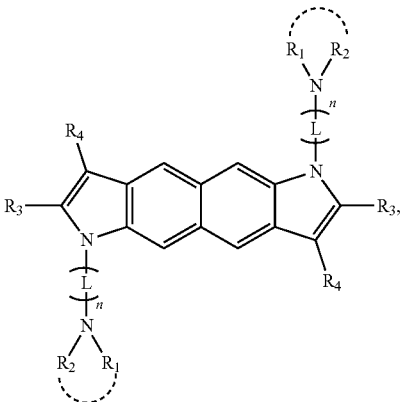

Formula II-11

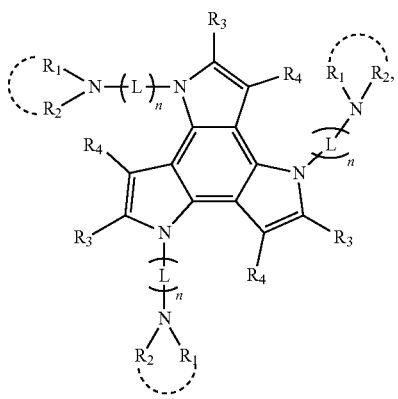

Formula II-12

Wherein $R_1$, $R_2$, $R_3$, $R_4$ and L each independently have the same range as defined in Formula I, n is 0 or 1.

In an embodiment, n is 1.

In an embodiment, L is any one selected from the group consisting of substituted or unsubstituted C6 to C20 (for example, C7, C9, C10, C12, C14, C15, C17 or C19, etc.) arylene and substituted or unsubstituted C3 to C20 (for example, C4, C6, C8, C10, C12, C14, C16 or C18, etc.) heteroarylene.

When a substituent is present in the above groups, the substituent is at least one selected from the group consisting of C1 to C10 (for example, C2, C3, C4, C5, C6, C7, C8 or C9) linear or branched alkyl, C6 to C20 (for example, C7, C9, C10, C12, C14, C15, C17 or C19, etc.) aryl and cyano.

In an embodiment, L is any one selected from the following groups, or any one of the following groups substituted with a substituent:

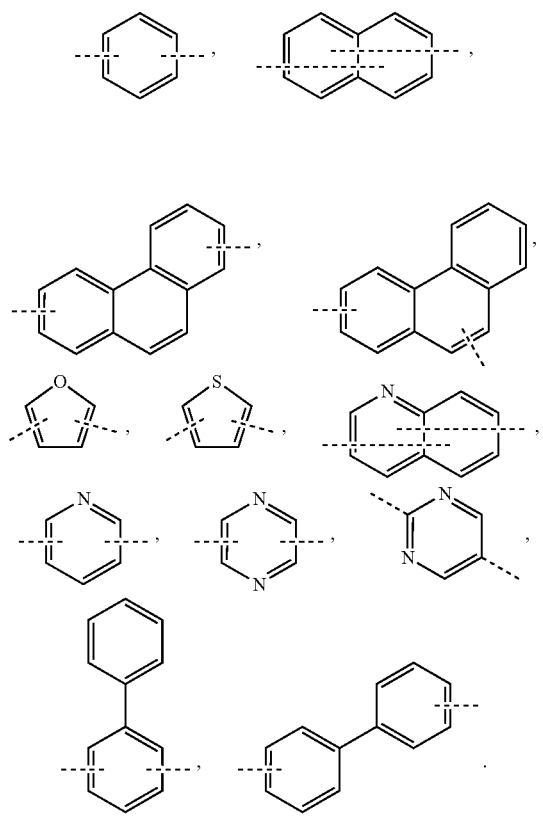

wherein the dashed line represents the linkage site of the group.

The substituent is at least one selected from the group consisting of C1 to C10 (for example, C2, C3, C4, C5, C6, C7, C8 or C9) linear or branched alkyl, C6 to C20 (for example, C7, C9, C10, C12, C14, C15, C17 or C19, etc.) aryl and cyano.

In an embodiment, $R_1$ and $R_2$ are each independently any one selected from the group consisting of substituted or unsubstituted C6 to C20 (for example, C7, C9, C10, C12, C14, C15, C17 or C19, etc.) aryl and substituted or unsubstituted C3 to C20 (for example, C4, C6, C8, C10, C12, C14, C16 or C18, etc.) heteroaryl, and $R_1$ and $R_2$ are not joined to each other or joined to form a ring.

When a substituent is present in the above groups, the substituent is at least one selected from the group consisting of C1 to C10 (for example, C2, C3, C4, C5, C6, C7, C8 or C9) linear or branched alkyl, C6 to C20 (for example, C7, C9, C10, C12, C14, C15, C17 or C19, etc.) aryl, C3 to C15 (for example, C4, C6, C8, C10, C12 or C14, etc.) heteroaryl and cyano.

In an embodiment, $R_1$ and $R_2$ are joined via a single bond to form a ring.

In an embodiment, $R_3$ and $R_4$ are each independently any one selected from the group consisting of C1 to C10 (for example, C2, C3, C4, C5, C6, C7, C8 or C9) linear or branched alkyl, C3 to C10 (for example, C4, C5, C6, C7, C8 or C9) cycloalkyl, C6 to C15 (for example, C7, C8, C9, C10, C11, C12, C13 or C14, etc.) arene and C3 to C15 (for example, C4, C6, C8, C10, C12, C13 or C14, etc.) heteroarene.

In an embodiment, the compound has a structure represented by Formula III-1 or Formula III-2:

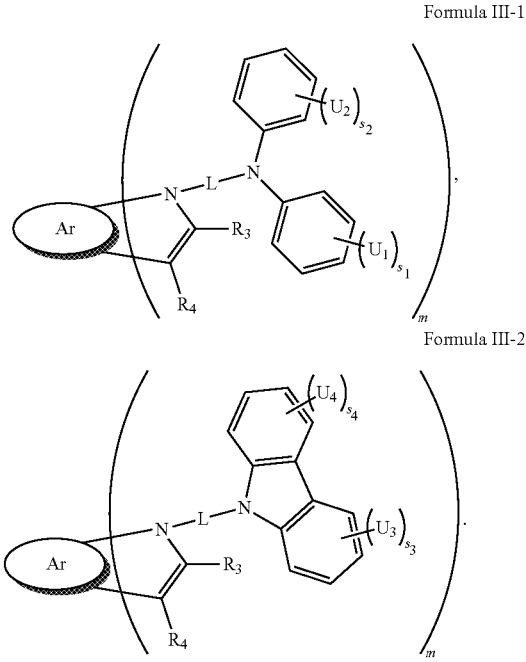

In Formula III-1 or Formula III-2, Ar, L and m each independently have the same range as defined in Formula I.

In Formula III-1 or Formula III-2, $U_1$, $U_2$, $U_3$ and $U_4$ are each independently any one selected from the group consisting of C1 to C10 (for example, C2, C3, C4, C5, C6, C7, C8 or C9) linear or branched alkyl, C6 to C20 (for example, C7, C9, C10, C12, C14, C15, C17 or C19, etc.) aryl, C3 to C20 (for example, C4, C6, C8, C10, C12, C14, C16 or C18, etc.) heteroaryl and cyano.

Here $s_1$ and $s_2$ are each independently an integer from 0 to 5, for example, 0, 1, 2, 3, 4 or 5; when $s_1$ is an integer from 2 to 5, adjacent $U_1$ substituents are not joined to each other or joined to form a ring; and when $s_2$ is an integer from 2 to 5, adjacent $U_2$ substituents are not joined to each other or joined to form a ring.

When the number Si of substituents $U_1$ is an integer from 2 to 5 (2, 3, 4 or 5), at least two $U_1$ substituents attached at adjacent positions of the benzene ring may not be joined to each other or be joined to form a ring. The specific joining and ring forming method is not limited in the present disclosure. Similarly, when the number $s_2$ of substituents $U_2$ is an integer from 2 to 5 (2, 3, 4 or 5), at least two $U_2$ substituents attached at adjacent positions of the benzene ring may not be joined to each other or be joined to form a ring. The specific joining and ring forming method is not limited in the present disclosure.

Here $s_3$ and $s_4$ are each independently an integer from 0 to 4, for example, 0, 1, 2, 3 or 4; when $s_3$ is an integer from 2 to 4, adjacent $U_3$ substituents are not joined to each other or joined to form a ring; and when $s_4$ is an integer from 2 to 4, adjacent $U_4$ substituents are not joined to each other or joined to form a ring.

When the number $s_3$ of substituents $U_3$ is an integer from 2 to 4 (2, 3 or 4), at least two $U_3$ substituents attached at adjacent positions of the benzene ring may not be joined to each other or be joined to form a ring. The specific joining and ring forming method is not limited in the present disclosure. Similarly, when the number $s_4$ of substituents $U_4$ is an integer from 2 to 4 (2, 3 or 4), at least two $U_4$ substituents attached at adjacent positions of the benzene ring may not be joined to each other or be joined to form a ring. The specific joining and ring forming method is not limited in the present disclosure.

In an embodiment, the compound is any one selected from the following compounds M1 to M65:

M1
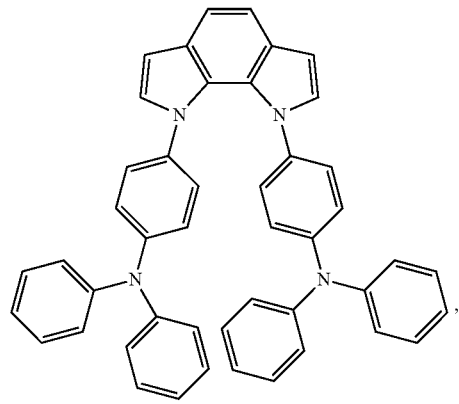

M2
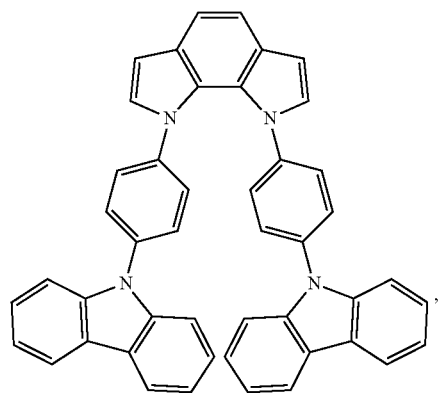

M3
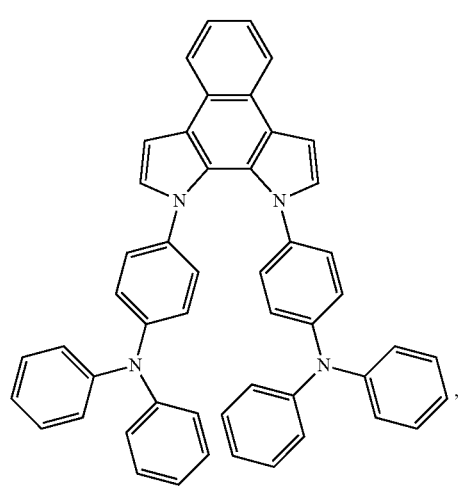

-continued

M4
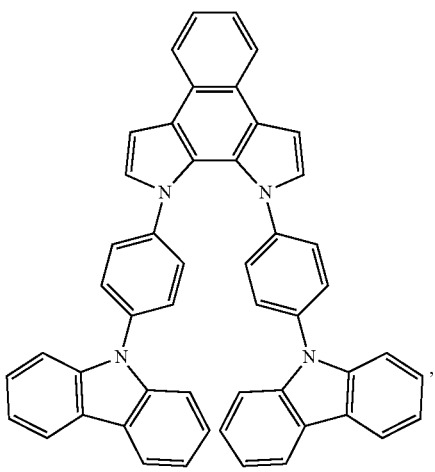

M5
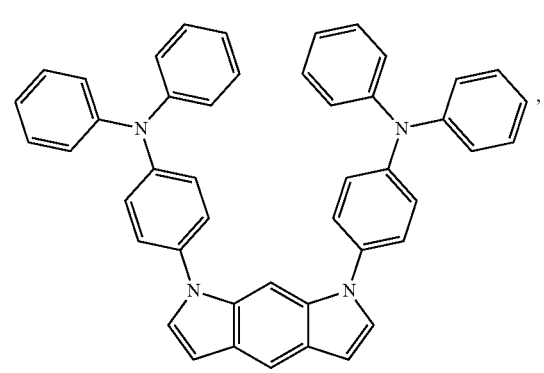

M6
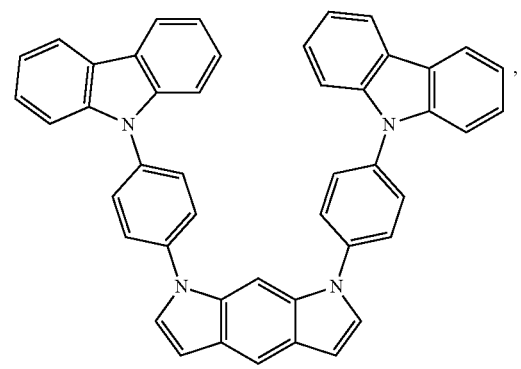

M7
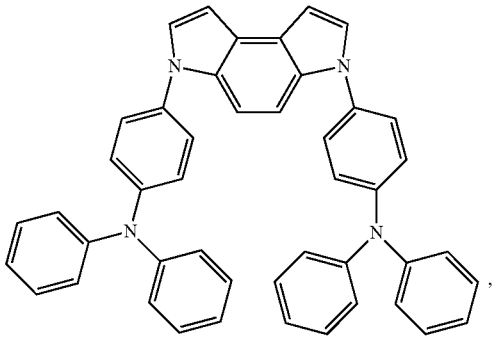

M8
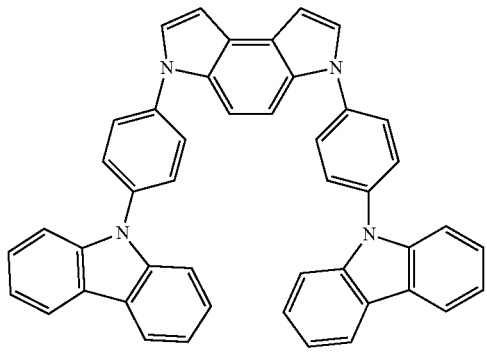
M11
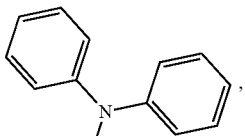
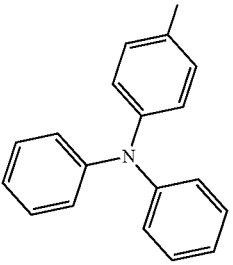
M9
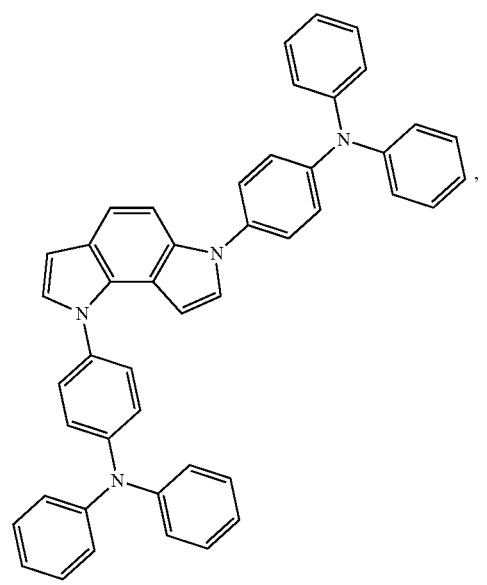
M12
M10
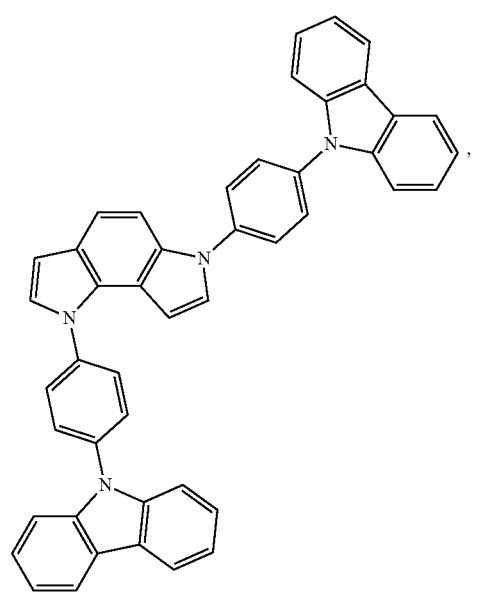
M13
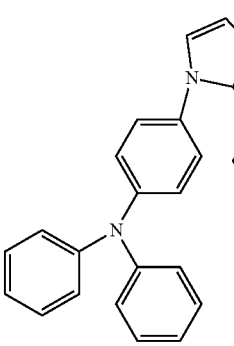
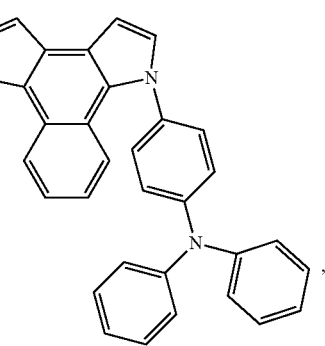

M14
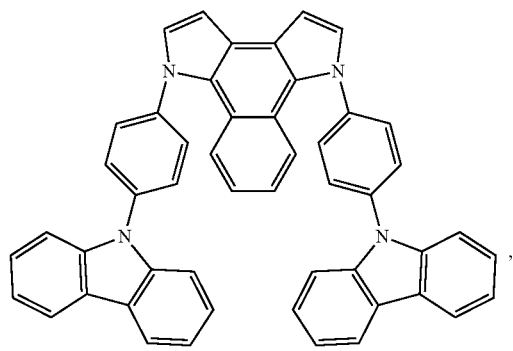
M15
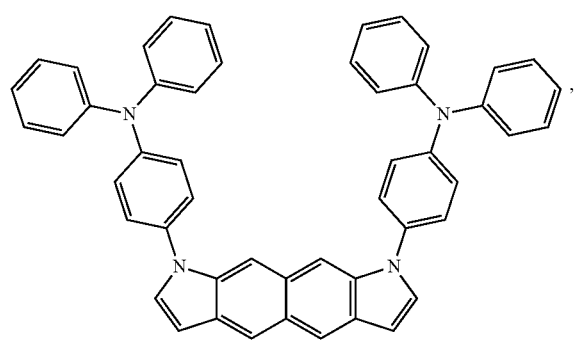
M16
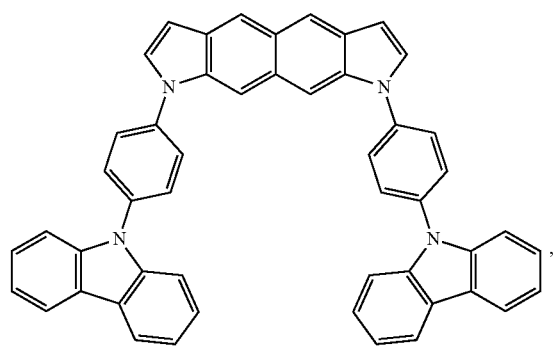
M17
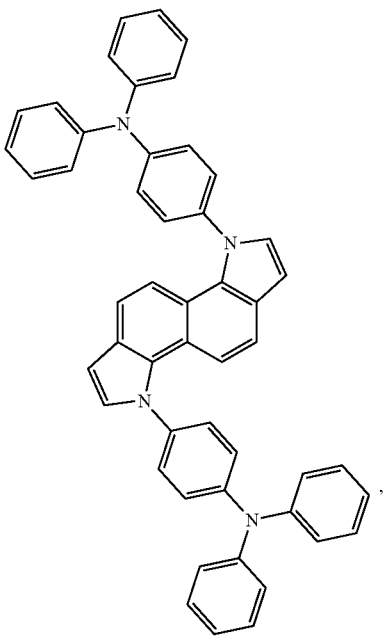
M18
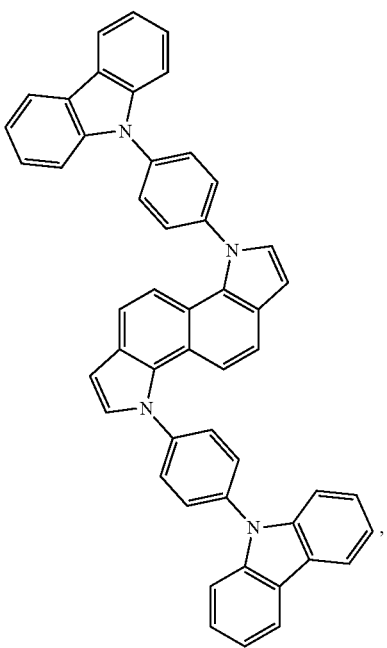

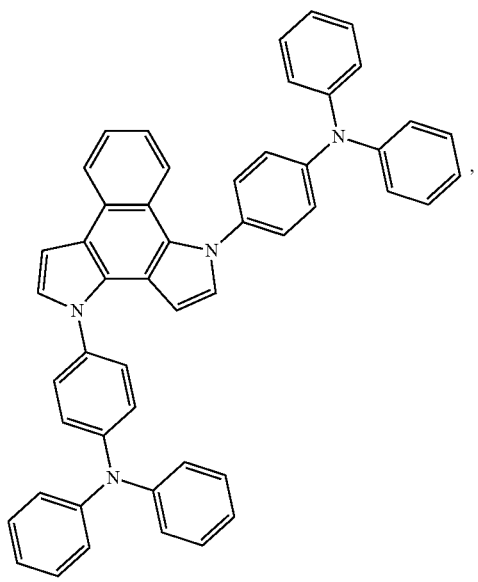
M19
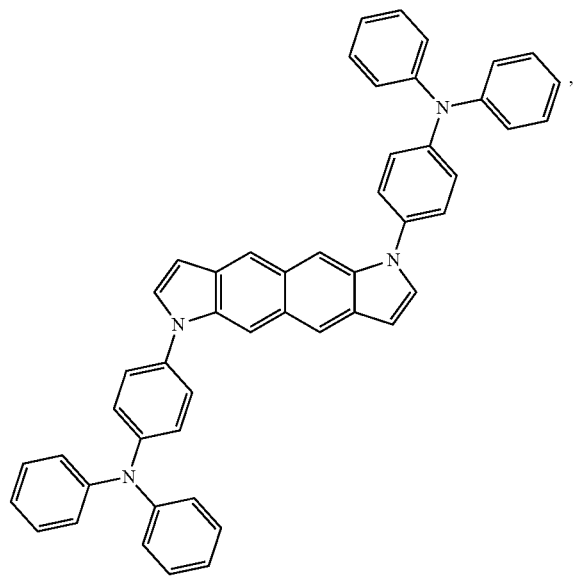
M21
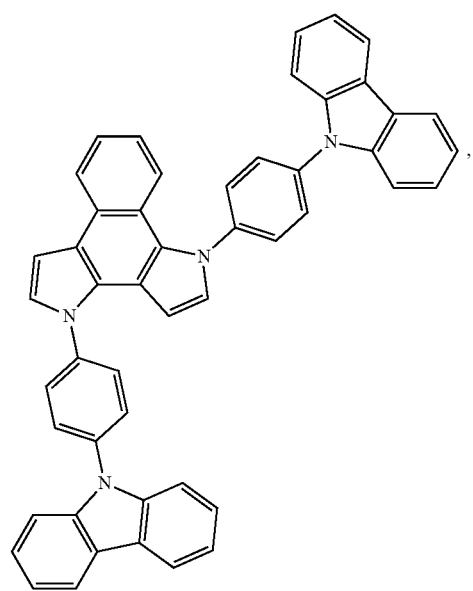
M20
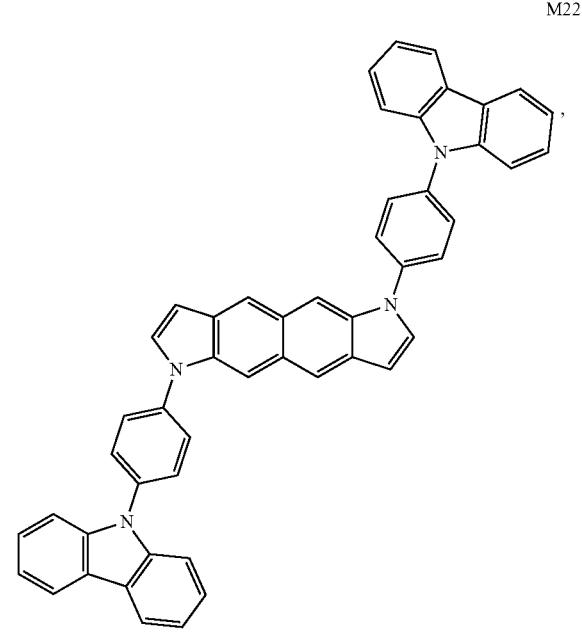
M22

M23
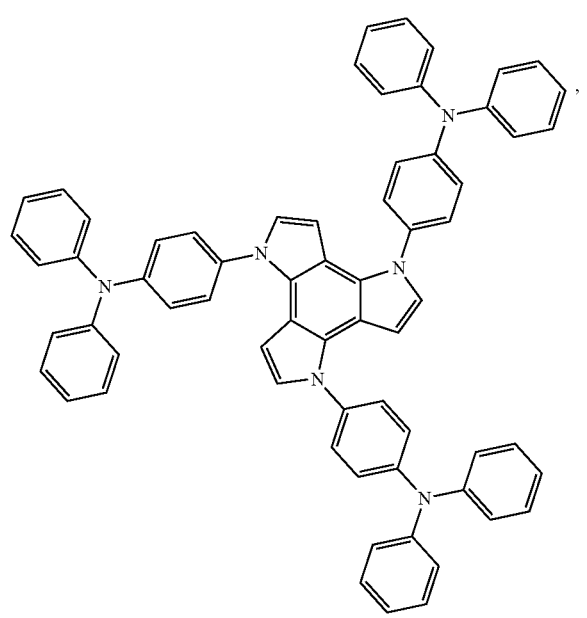
M25
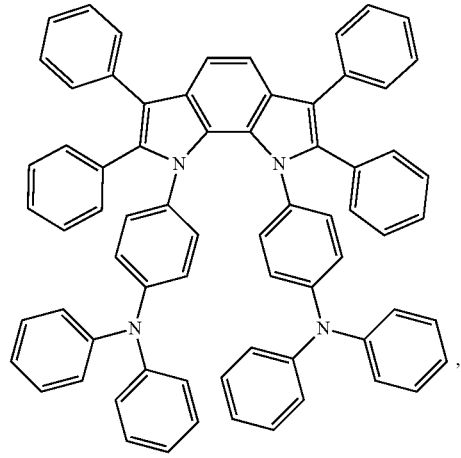
M26
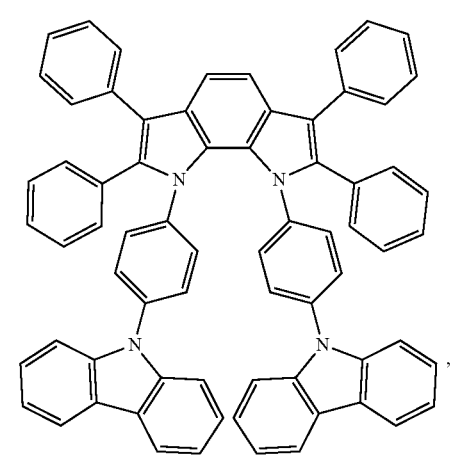
M24
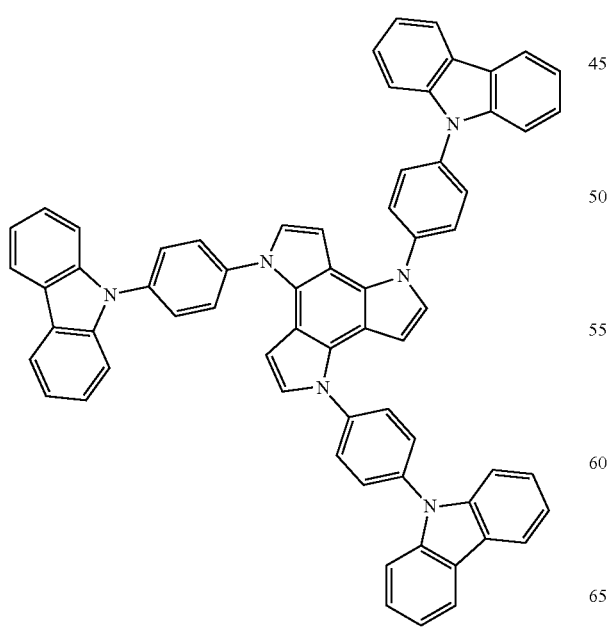
M27
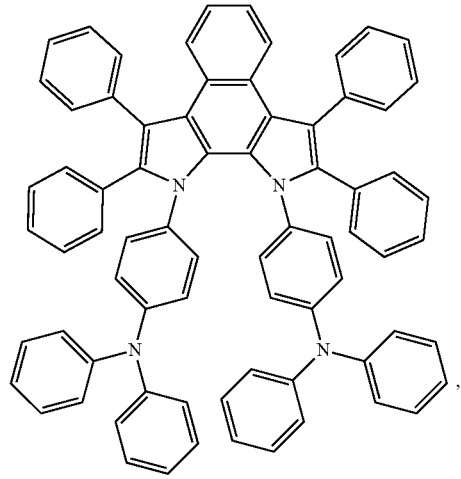

M28
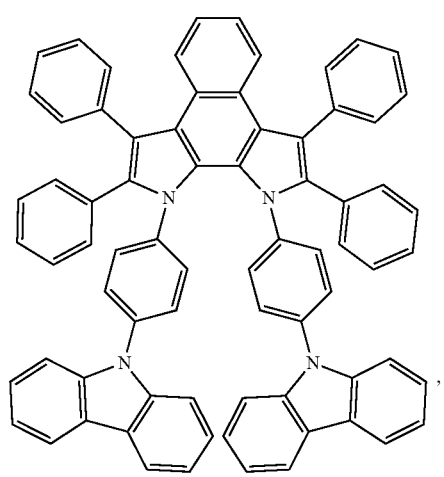
M29
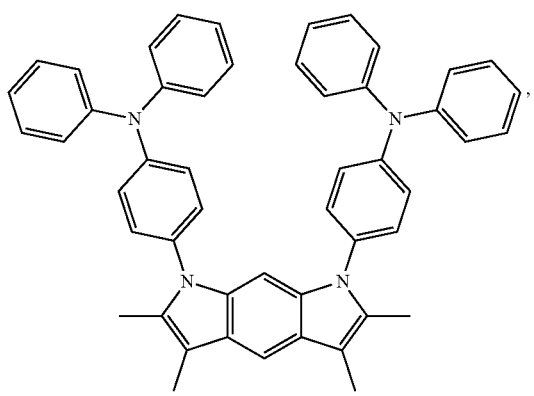
M30
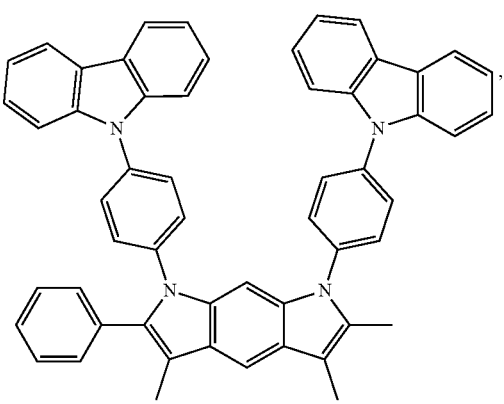
M31
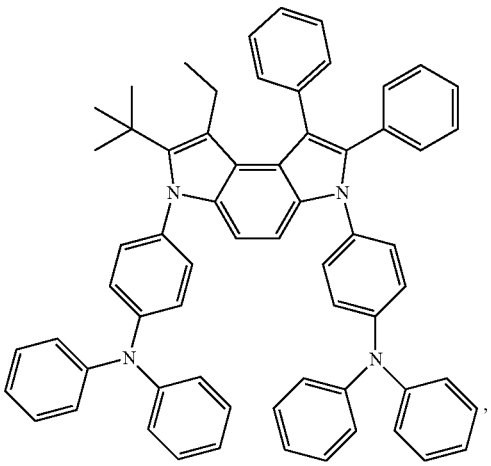
M32
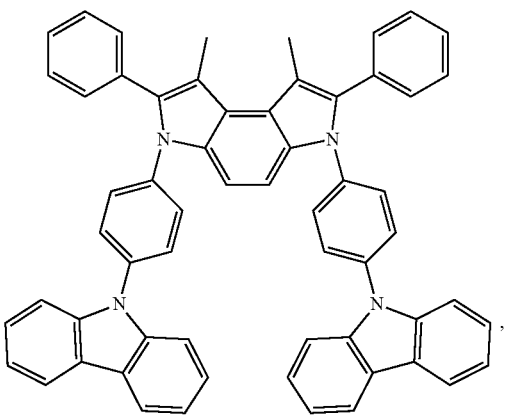
M33
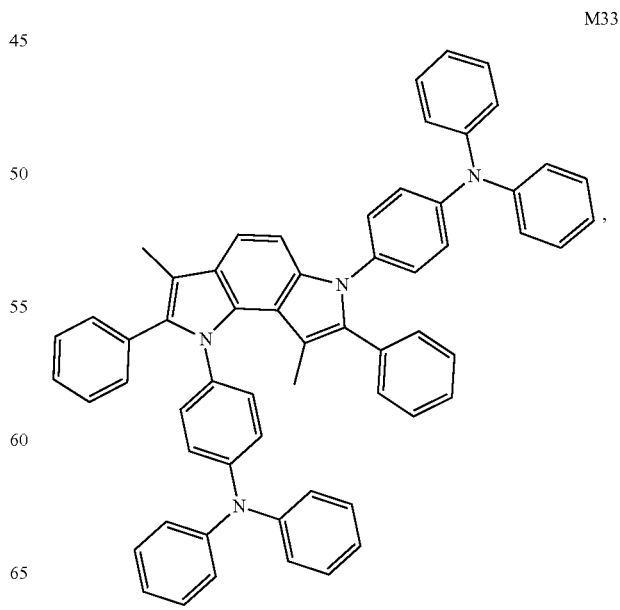

M34
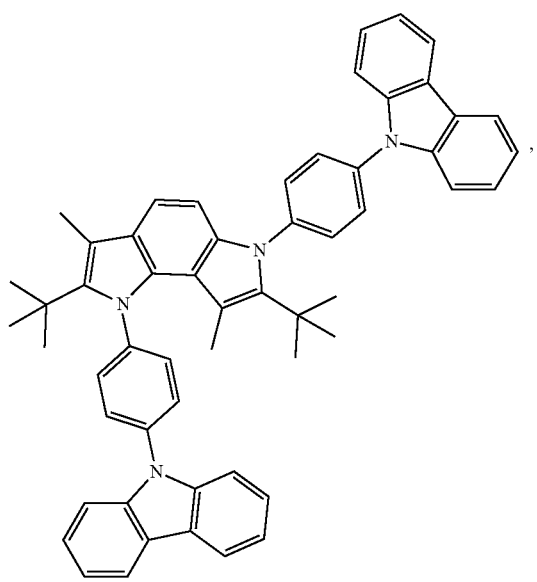
M35
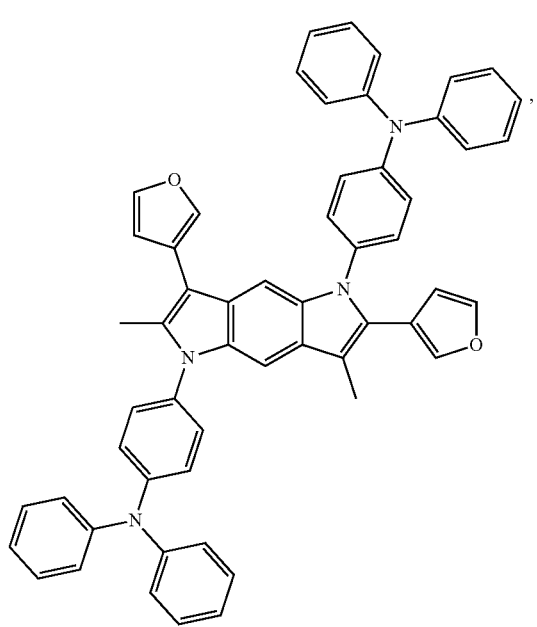
M36
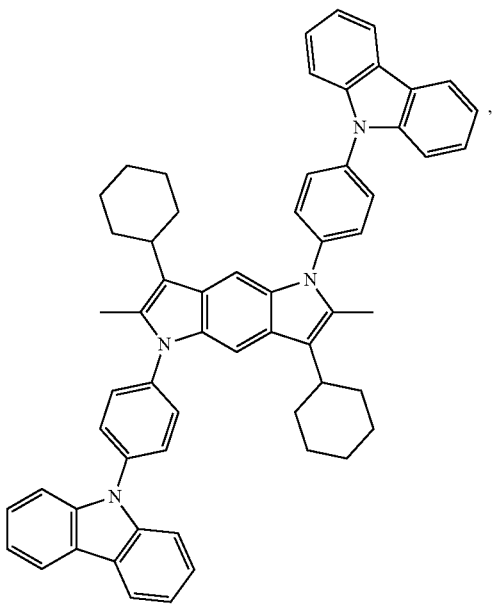
M37
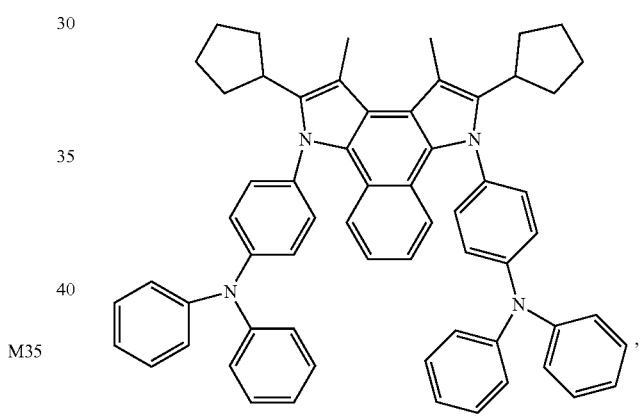
M38
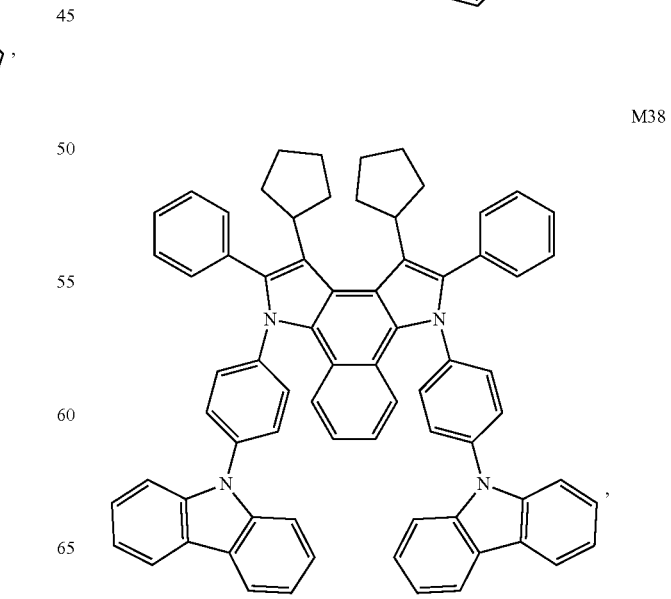

-continued
M39
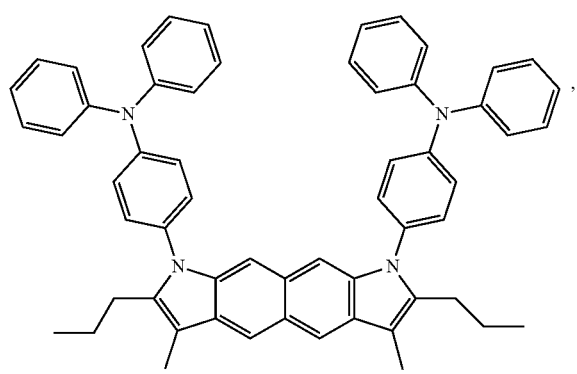
M40
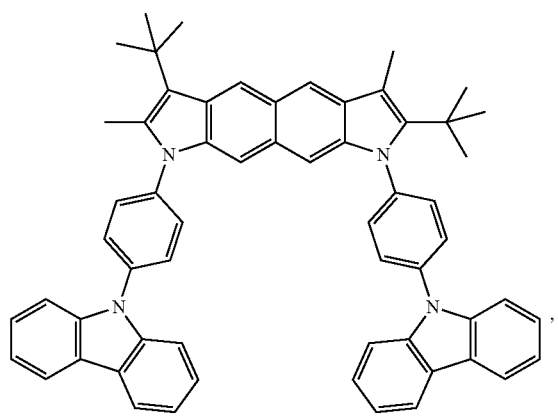
M41
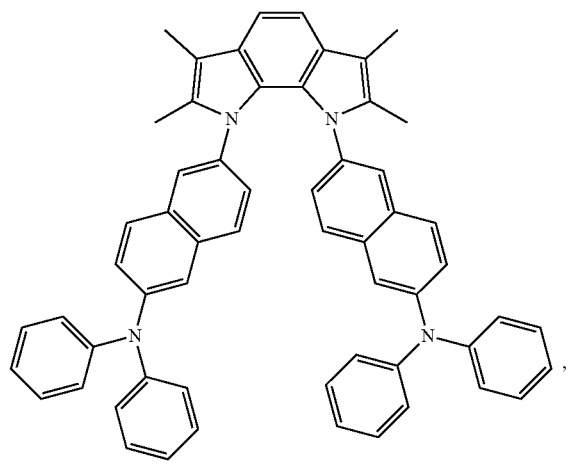
-continued
M42
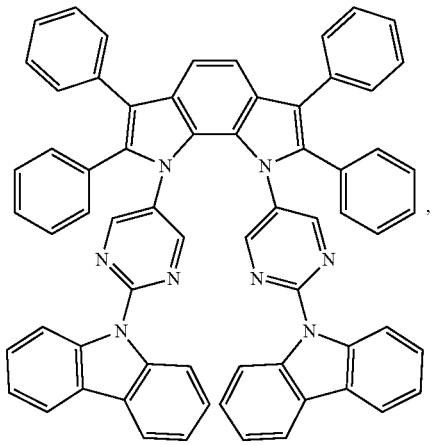
M43
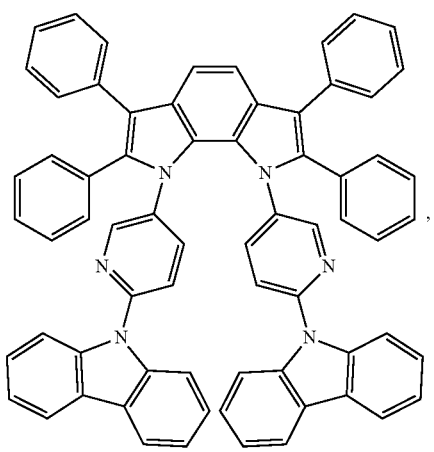
M44
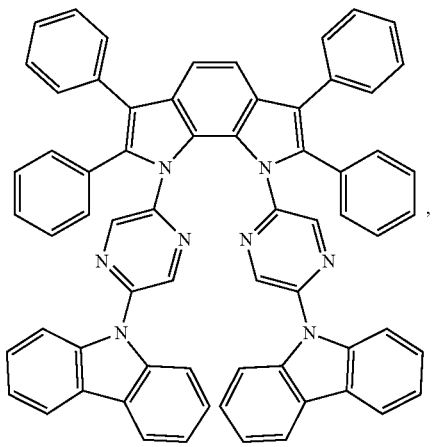

M45
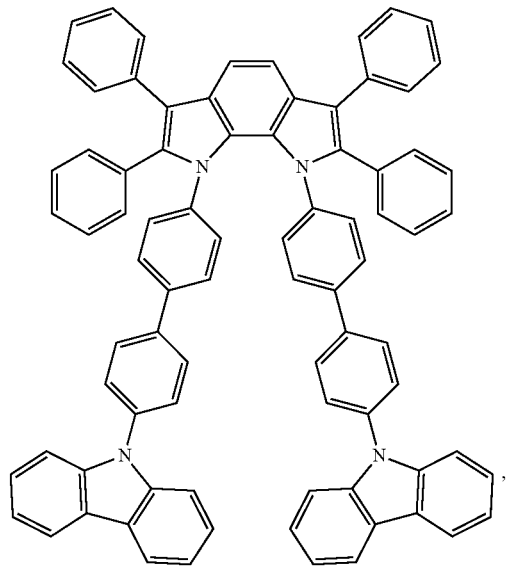
M46
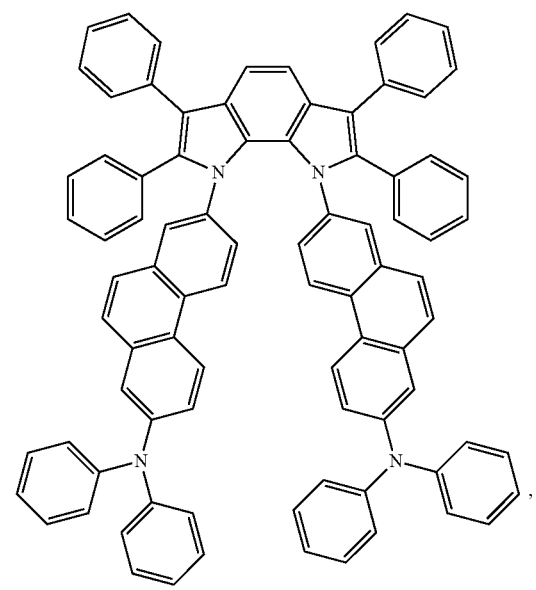
M47
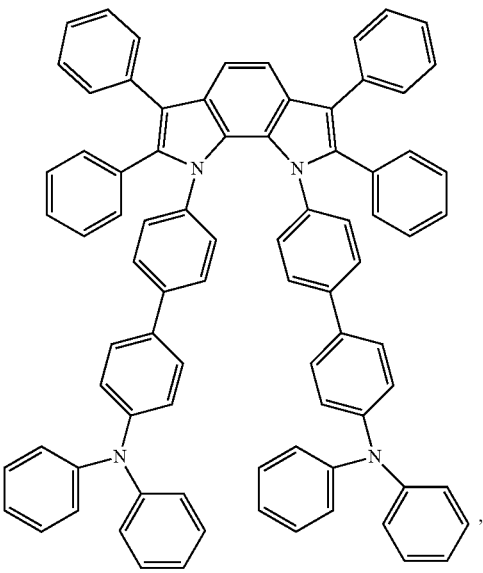
M48
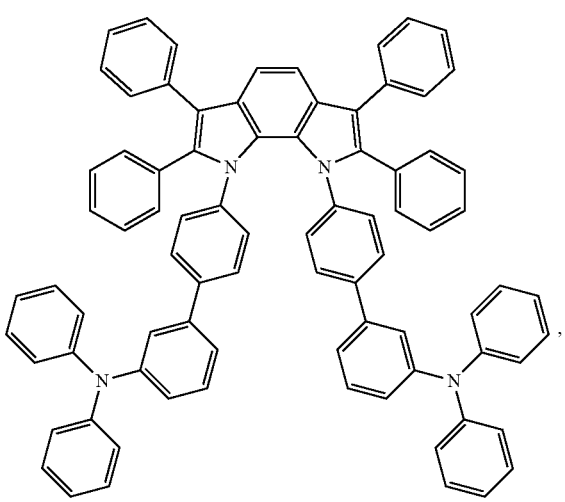
M49
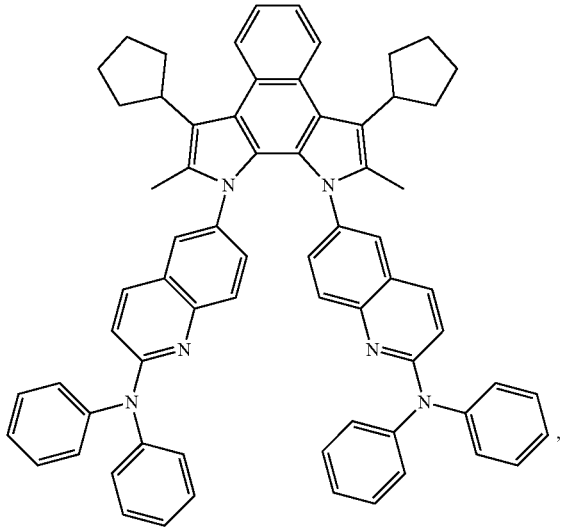

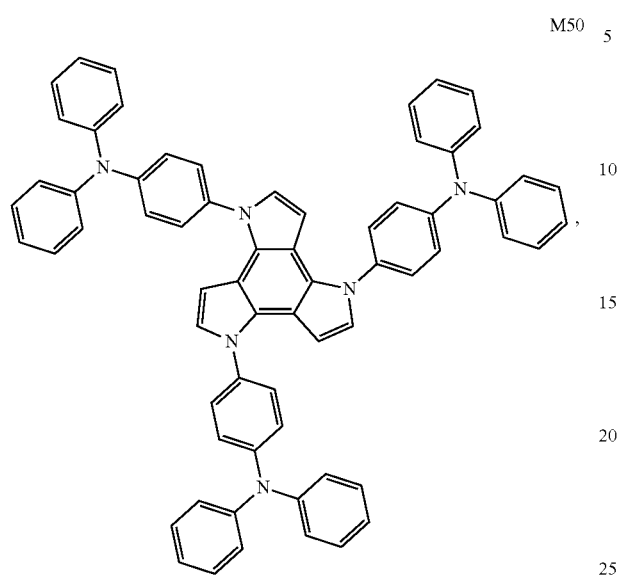
M50
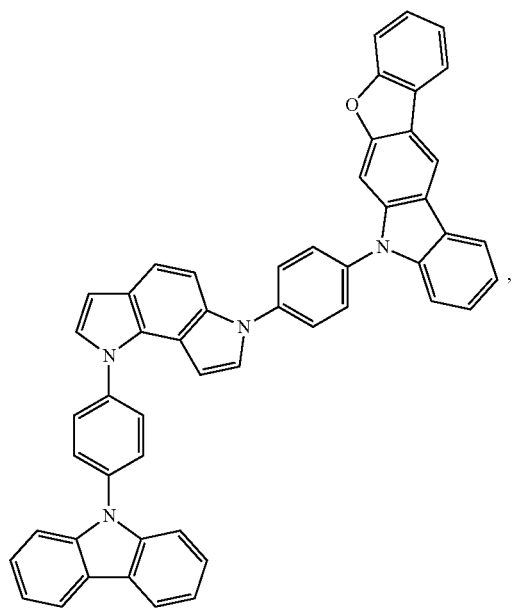
M52
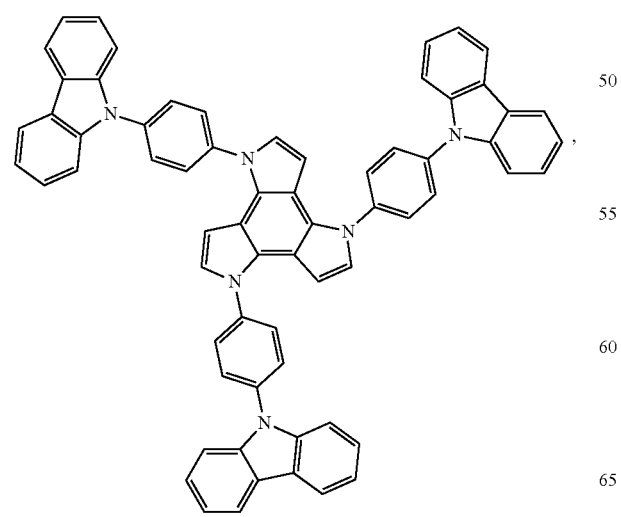
M51
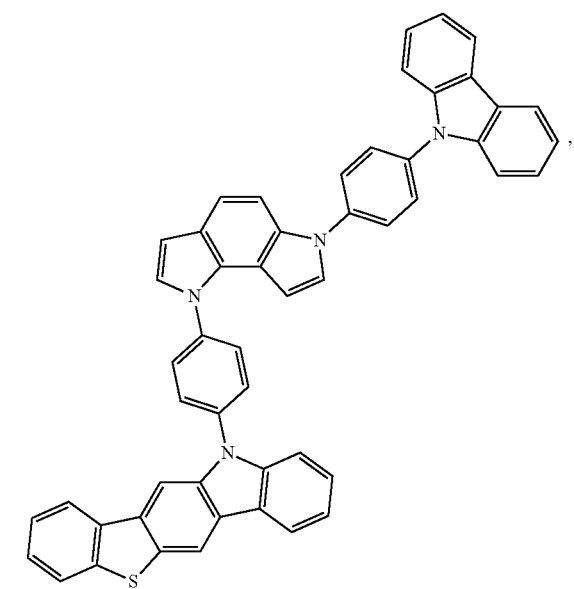
M53

-continued
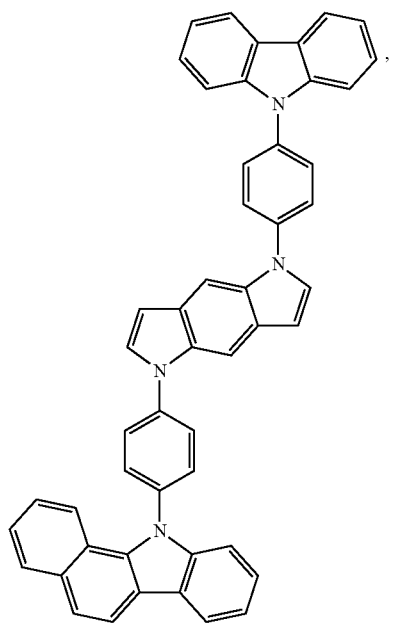
M54
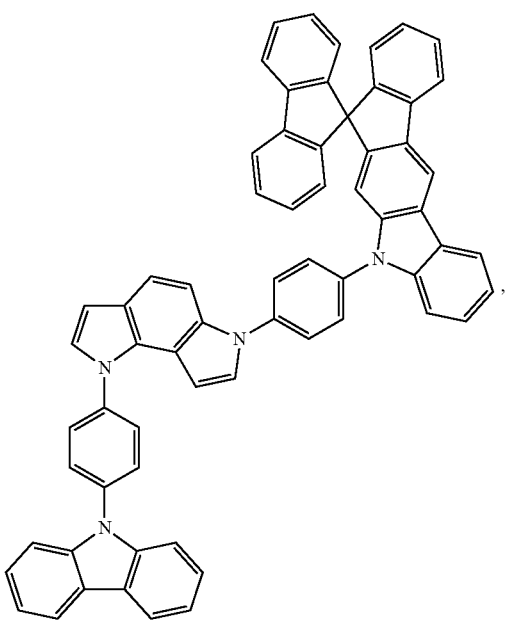
M56
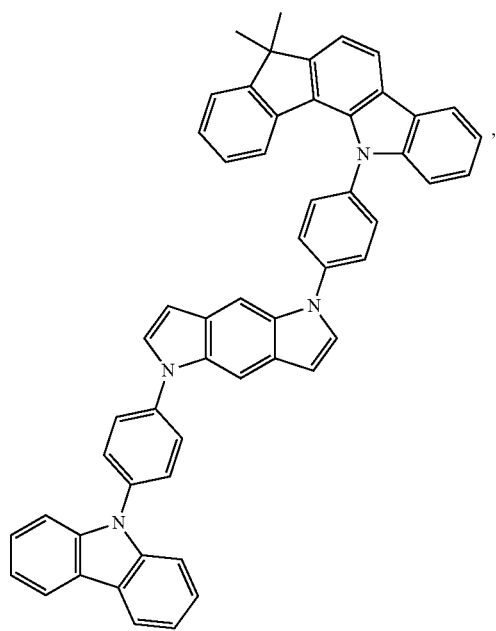
M55
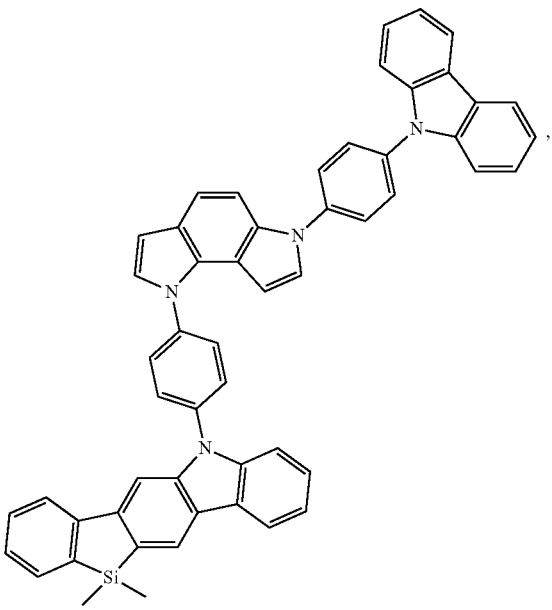
M57

M58
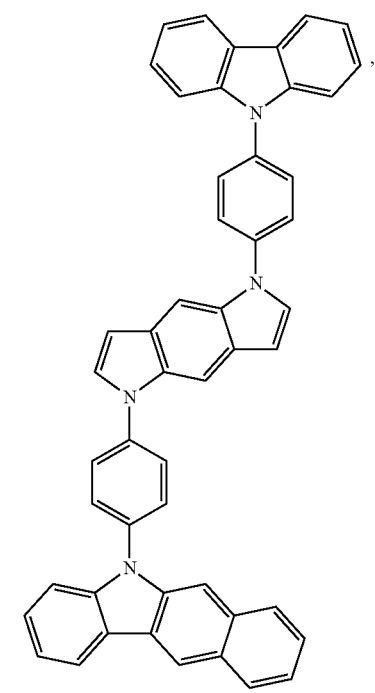
M60
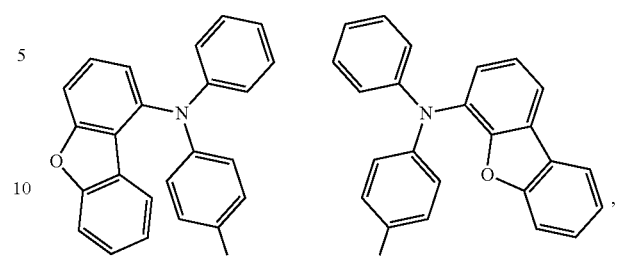
M61
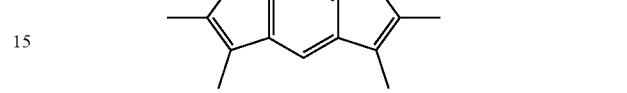
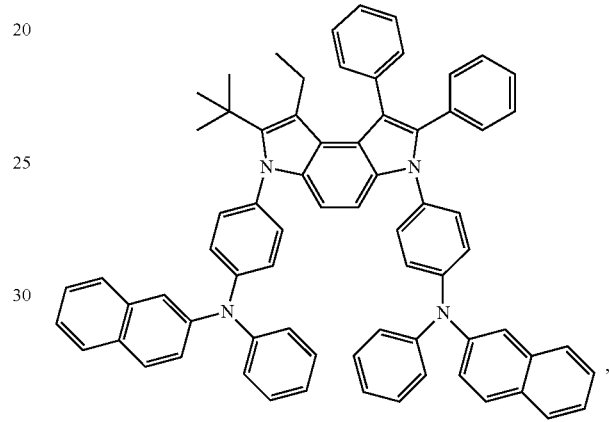
M62
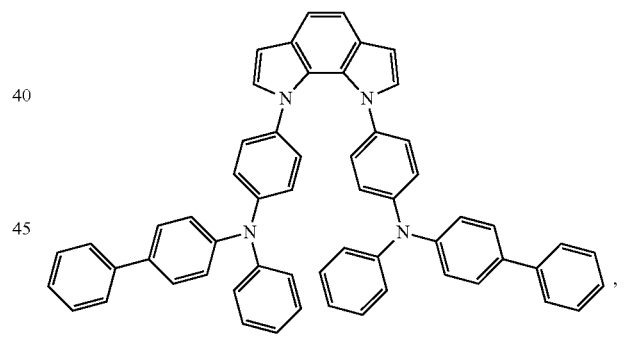
M59
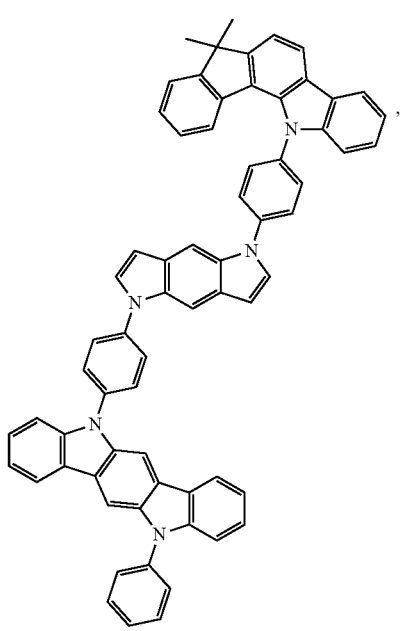
M63
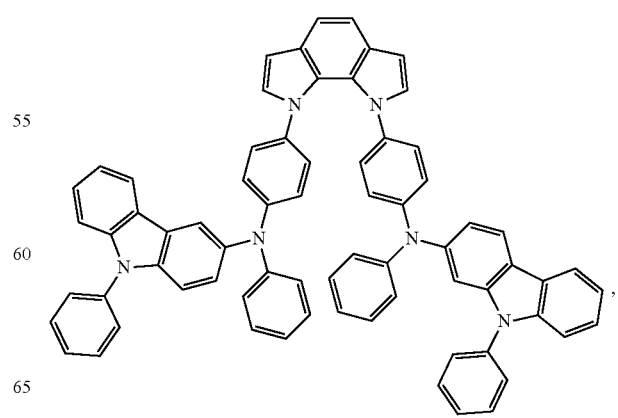

M64

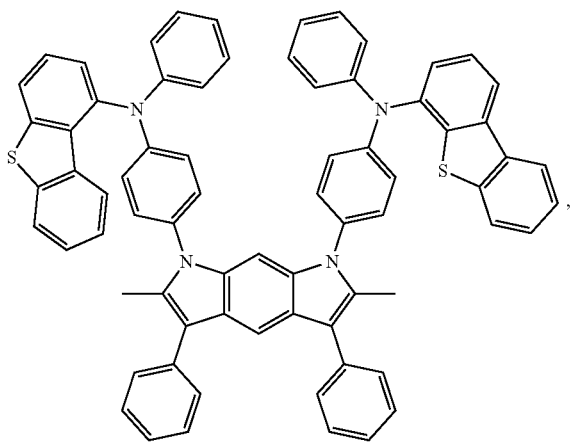

M65

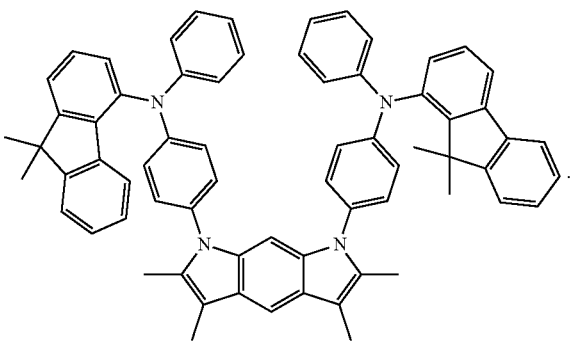

In another aspect, the present disclosure provides an organic electroluminescent device, including an anode, a cathode and an organic thin film layer disposed between the anode and the cathode, wherein the organic thin film layer includes a hole transport layer, and the hole transport layer includes the compound described above.

The organic electroluminescent device includes an anode, a cathode and at least one organic thin film layer disposed between the anode and the cathode. The organic thin film layer includes any one or a combination of at least two selected from the group consisting of a light emitting layer, a hole transport layer, a hole injection layer, an electron blocking layer, a hole blocking layer, an electron transport layer and an electron injection layer.

In the organic electroluminescent device of the present disclosure, the material of the anode may be a metal, a metal oxide or a conductive polymer. The metal includes copper, gold, silver, iron, chromium, nickel, manganese, palladium and platinum, etc. as well as alloys thereof. The metal oxide includes indium tin oxide (ITO), indium zinc oxide (IZO), zinc oxide, indium gallium zinc oxide (IGZO), etc. The conductive polymer includes polyaniline, polypyrrole and poly(3-methylthiophene), etc. In addition to the above materials that facilitate hole injection and combinations thereof, further included are known materials that are suitable for use as an anode.

In the organic electroluminescent device, the material of the cathode may be a metal or a multilayer metal material. The metal includes aluminum, magnesium, silver, indium, tin and titanium, etc. as well as alloys thereof. The multilayer metal material includes LiF/Al, LiO$_2$/Al and BaF$_2$/Al, etc. In addition to the above materials that facilitate electron injection and combinations thereof, further included are known materials that are suitable for use as a cathode.

In the organic electroluminescent device, the organic thin film layer includes at least one light emitting layer (EML) and any one or a combination of at least two selected from the group consisting of a hole transport layer (HTL), a hole injection layer (HIL), an electron blocking layer (EBL), a hole blocking layer (HBL), an electron transport layer (ETL) and an electron injection layer (EIL) which is(are) disposed on two sides of the light emitting layer, wherein the hole/electron injection and transport layers may be carbazole compounds, arylamine compounds, benzimidazole compounds and metal compounds, etc.

A schematic diagram of the organic electroluminescent device is shown in FIG. 1. The organic electroluminescent device includes an anode 101, a cathode 102, a light emitting layer 103 disposed between the anode 101 and the cathode 102, and a first organic thin film layer 104 and a second organic thin film layer 105 which are disposed on two sides of the light emitting layer 103, separately. The first organic thin film layer 104 includes any one or a combination of at least two selected from the group consisting of a hole transport layer (HTL), a hole injection layer (HIL), an electron blocking layer (EBL), a hole blocking layer (HBL), an electron transport layer (ETL) and an electron injection layer (EIL). The second organic thin film layer 105 includes any one or a combination of at least two selected from the group consisting of a hole transport layer (HTL), a hole injection layer (HIL), an electron blocking layer (EBL), a hole blocking layer (HBL), an electron transport layer (ETL) and an electron injection layer (EIL).

The organic electroluminescent device may be prepared by the following method: forming an anode on a transparent or opaque smooth substrate, forming an organic thin film layer on the anode, and forming a cathode on the organic thin film layer. The organic thin layer may be formed by using known film forming methods such as evaporation, sputtering, spin coating, impregnation and ion plating.

In an embodiment, the cathode is covered with a cap layer, wherein the cap layer has a refractive index of 1.85 to 2.05, for example, 1.86, 1.88, 1.9, 1.92, 1.94, 1.95, 1.97, 1.99, 2, 2.01, 2.03 or 2.04, etc.

In an embodiment, the cap layer includes the compound described above.

In another aspect, the present disclosure provides an electronic apparatus, including the organic electroluminescent device described above.

The compound having the structure represented by Formula I in the present disclosure is exemplarily prepared according to the following synthesis route:

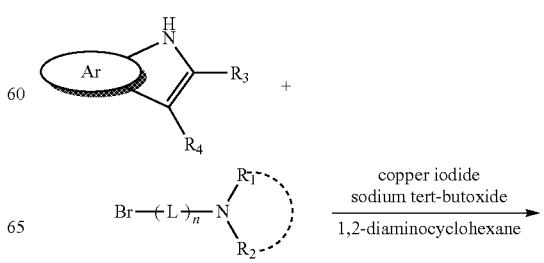

-continued

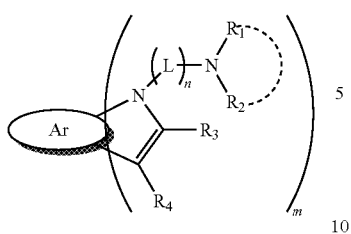

wherein $R_1$, $R_2$, $R_3$, $R_4$, L, n, m and Ar each independently have the same range as defined in Formula I.

Example 1

This example provides a compound whose structure is as follows:

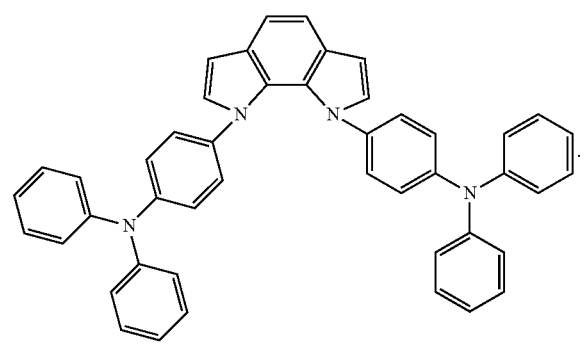

M1

The synthesis route of the compound is as follows:

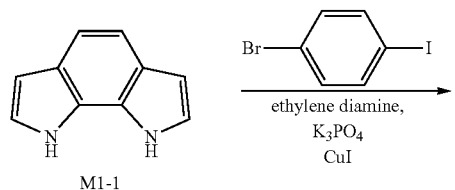

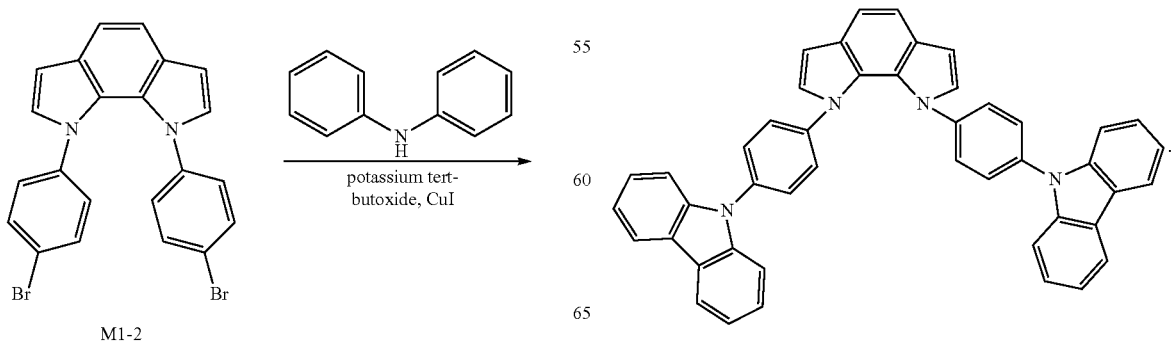

M1

The specific preparation method includes steps described below:

(1) In a 250 mL round-bottom flask, compound M1-1 (15 mmol), p-bromoiodobenzene (15 mmol), $K_3PO_4$ (15 mmol), ethylene diamine (1.5 mL) and CuI (30 mmol) were added to toluene (100 mL), and the mixture was stirred at 120° C. for 3 hours. The reaction mixture was separated with ethyl acetate/distilled water, removed for water with $MgSO_4$ and then distilled under reduced pressure. The product was subjected to column chromatography using a mixed solvent of dichloromethane and hexane to obtain an intermediate M1-2.

(2) In a 250 mL round-bottom flask, M1-2 (15 mmol), CuI (15 mmol), potassium tert-butoxide (65 mmol), 1,2-diaminocyclohexane (12 mmol) and diarylamine (35 mmol) were added to dry 1,4-dioxane (400 mL), and the mixture was refluxed under a $N_2$ atmosphere for 48 hours. The obtained reaction solution was cooled to room temperature, added to water, filtered through a celite pad, extracted with dichloromethane, washed with water, dried with anhydrous magnesium sulfate, filtered and evaporated. The crude product was purified through silica gel column chromatography to obtain a target product M1.

The structure of M1 was tested: theoretical values of an elemental analysis of the structure: C 85.98, H 5.30, N 8.72; test values: C 85.98, H 5.30, N 8.72.

Matrix-assisted laser desorption ionization time-of-flight mass spectrometry (MALDI-TOF-MS) (m/z): theoretical calculation values: $C_{46}H_{34}N_4$, 642.28; test value: 642.27.

Example 2

This example provides a compound whose structure is as follows:

M2

39

The synthesis route of the compound is as follows:

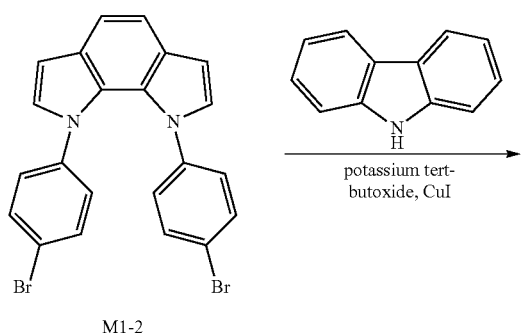

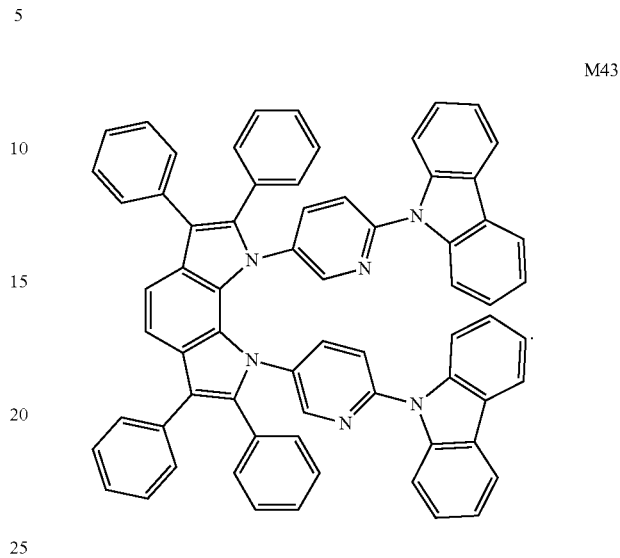

M2

The specific preparation method is described below:

In a 250 mL round-bottom flask, M1-2 (15 mmol), CuI (15 mmol), potassium tert-butoxide (65 mmol), 1,2-diaminocyclohexane (12 mmol) and 9H carbazole (35 mmol) were added to dry 1,4-dioxane (400 mL), and the mixture was refluxed under a N$_2$ atmosphere for 48 hours. The obtained reaction solution was cooled to room temperature, added to water, filtered through a celite pad, extracted with dichloromethane, washed with water, dried with anhydrous magnesium sulfate, filtered and evaporated. The crude product was purified through silica gel column chromatography to obtain a target product M2.

The structure of M2 was tested: theoretical values of an elemental analysis of the structure: C 86.52, H 4.70, N 8.78; test values: C 86.52, H 4.70, N 8.78.

Matrix-assisted laser desorption ionization time-of-flight mass spectrometry (MALDI-TOF-MS) (m/z): theoretical calculation values: $C_{46}H_{30}N_4$, 638.25; test value: 638.24.

40

Example 3

This example provides a compound whose structure is as follows:

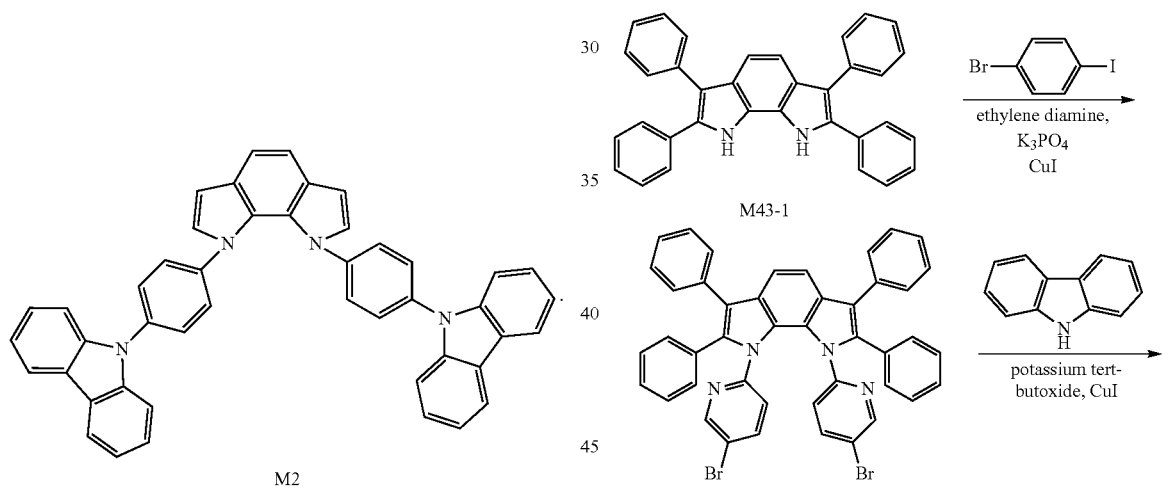

The synthesis route of the compound is as follows:

The specific preparation method includes steps described below:

(1) In a 250 mL round-bottom flask, M43-1 (15 mmol), p-bromoiodobenzene (35 mmol), K₃PO₄ (15 mmol), ethylene diamine (1.5 mL) and CuI (30 mmol) were added to toluene (100 mL), and the mixture was stirred at 120° C. for 3 hours. The reaction mixture was separated with ethyl acetate/distilled water, removed for water with MgSO₄, and then distilled under reduced pressure. The product was subjected to column chromatography using a mixed solvent of dichloromethane and hexane to obtain an intermediate M43-2.

(2) In a 250 mL round-bottom flask, M43-2 (15 mmol), CuI (15 mmol), potassium tert-butoxide (65 mmol), 1,2-diaminocyclohexane (12 mmol) and 9H carbazole (35 mmol) were added to dry 1,4-dioxane (400 mL), and the mixture was refluxed under a $N_2$ atmosphere for 48 hours. The obtained reaction solution was cooled to room temperature, added to water, filtered through a celite pad, extracted with dichloromethane, washed with water, dried with anhydrous magnesium sulfate, filtered and evaporated. The crude product was purified through silica gel column chromatography to obtain a target product M43.

The structure of M43 was tested: theoretical values of an elemental analysis of the structure: C 86.44, H 4.66, N 8.90; test values: C 86.44, H 4.66, N 8.90.

Matrix-assisted laser desorption ionization time-of-flight mass spectrometry (MALDI-TOF-MS) (m/z): theoretical calculation values: $C_{68}H_{44}N_6$, 944.36; test value: 944.35.

Example 4

This example provides a compound whose structure is as follows:

M50

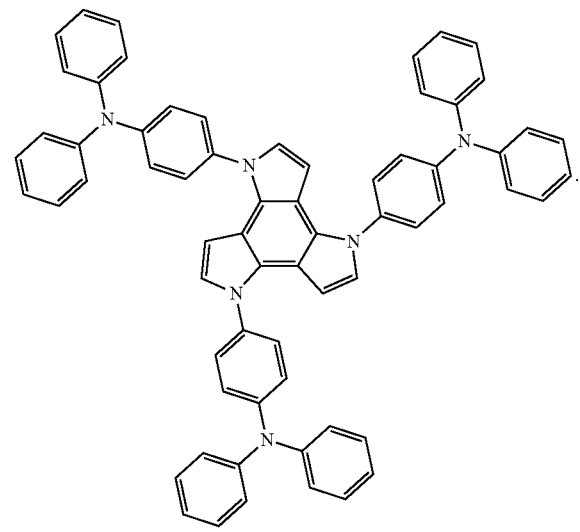

The synthesis route of the compound is as follows:

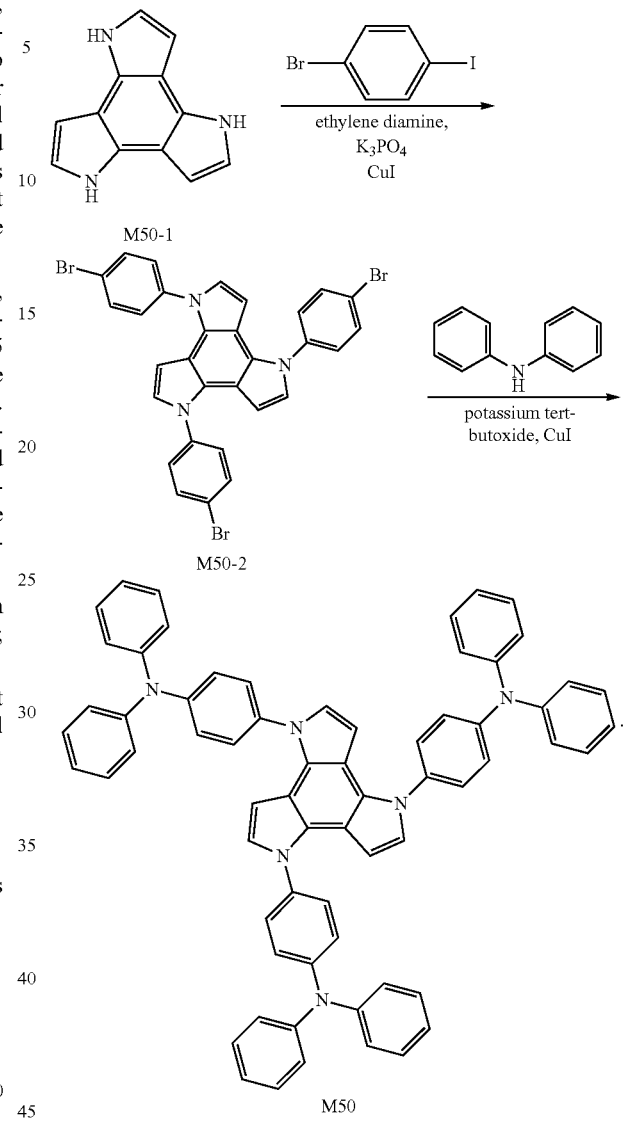

The specific preparation method includes steps described below:

(1) In a 250 mL round-bottom flask, M50-1 (15 mmol), p-bromoiodobenzene (45 mmol), K₃PO₄ (15 mmol), ethylene diamine (1.5 mL) and CuI (30 mmol) were added to toluene (100 mL), and the mixture was stirred at 120° C. for 3 hours. The reaction mixture was separated with ethyl acetate/distilled water, removed for water with MgSO₄, and then distilled under reduced pressure. The product was subjected to column chromatography using a mixed solvent of dichloromethane and hexane to obtain an intermediate M50-2.

(2) In a 250 mL round-bottom flask, M50-2 (15 mmol), CuI (15 mmol), potassium tert-butoxide (65 mmol), 1,2-diaminocyclohexane (12 mmol) and diarylamine (50 mmol) were added to dry 1,4-dioxane (400 mL), and the mixture was refluxed under a $N_2$ atmosphere for 48 hours. The obtained reaction solution was cooled to room temperature, added to water, filtered through a celite pad, extracted with dichloromethane, washed with water, dried with anhydrous magnesium sulfate, filtered and evaporated. The crude product was purified through silica gel column chromatography to obtain a target product M50.

The structure of M50 was tested: theoretical values of an elemental analysis of the structure: C 85.71, H 5.19, N 9.09; test values: C 85.71, H 5.19, N 9.09.

Matrix-assisted laser desorption ionization time-of-flight mass spectrometry (MALDI-TOF-MS) (m/z): theoretical calculation values: $C_{66}H_{48}N_6$, 924.39; test value: 924.38.

Example 5

This example provides a compound whose structure is as follows:

M60

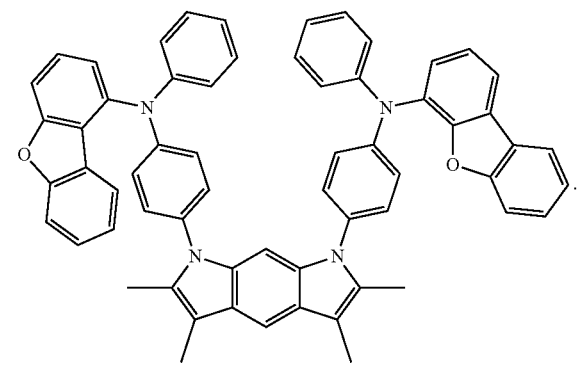

The synthesis route of the compound is as follows:

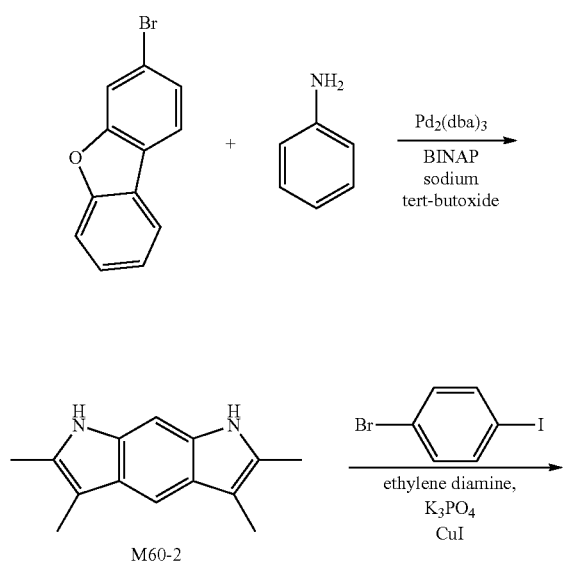

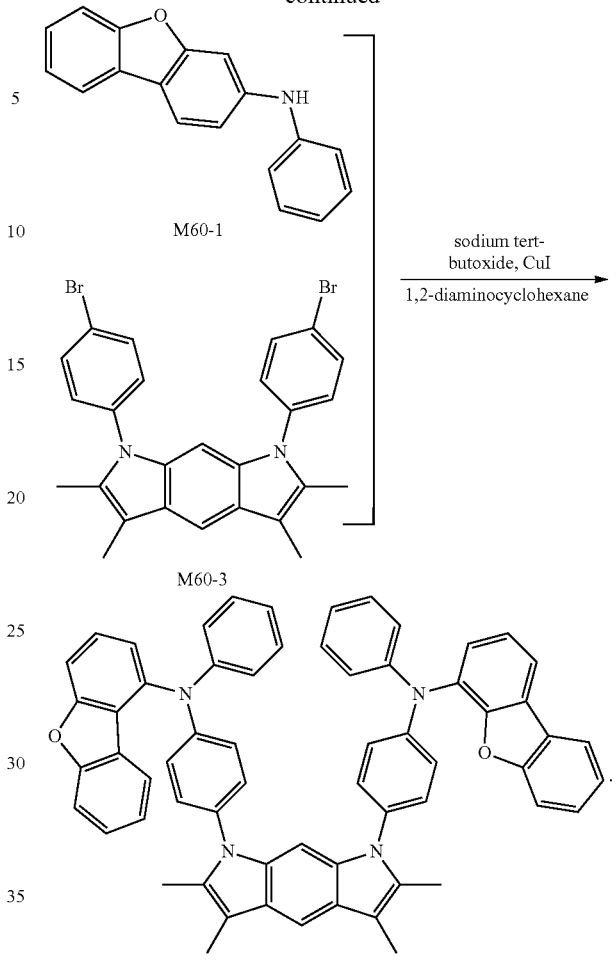

The specific preparation method includes steps described below:

(1) In a 250 mL round-bottom flask, 3-bromo-dibenzofuran (15 mmol), aniline (15 mmol), 10 mol % tris(dibenzalacetone)dipalladium(0) $Pd_2(dba)_3$, sodium tert-butoxide (100 mmol), (±)-2,2'-bis-(diphenylphosphino)-1,1'-binaphtyl (BINAP, 4 mmol) were added to dry toluene (100 mL), and the mixture was refluxed under a $N_2$ atmosphere for 48 hours. The obtained intermediate was cooled to room temperature, added to water, and filtered through a celite pad. The filtrate was extracted with dichloromethane, washed with water, dried with anhydrous magnesium sulfate, filtered and evaporated. The crude product was purified through silica gel column chromatography to obtain an intermediate dibenzofuran-3-yl-phenyl-amine M60-1.

(2) In a 250 mL round-bottom flask, M60-2 (15 mmol), p-bromoiodobenzene (15 mmol), $K_3PO_4$ (15 mmol), ethylene diamine (1.5 mL) and CuI (30 mmol) were added to toluene (100 mL), and the mixture was stirred at 120° C. for 3 hours. The reaction mixture was separated with ethyl acetate/distilled water, removed for water with $MgSO_4$, and then distilled under reduced pressure. The product was subjected to column chromatography using a mixed solvent of dichloromethane and hexane to obtain an intermediate M60-3.

(3) In a 250 mL round-bottom flask, M60-1 (30 mmol), M60-3 (15 mmol), CuI (15 mmol), potassium tert-butoxide (65 mmol) and 1,2-diaminocyclohexane (12 mmol) were added to dry 1,4-dioxane (400 mL), and the mixture was refluxed under a $N_2$ atmosphere for 48 hours. The obtained reaction solution was cooled to room temperature, added to water, filtered through a celite pad, extracted with dichloromethane, washed with water, dried with anhydrous magnesium sulfate, filtered and evaporated. The crude product was purified through silica gel column chromatography to obtain a target product M60.

The structure of M60 was tested: theoretical values of an elemental analysis of the structure: C 84.74, H 5.24, N 6.38, O 3.64; test values: C 84.74, H 5.24, N 6.38, O 3.64.

Matrix-assisted laser desorption ionization time-of-flight mass spectrometry (MALDI-TOF-MS) (m/z): theoretical calculation values: $C_{62}H_{46}N_4O_2$, 878.36; test value: 878.35.

Application Example 1

This application example provides an organic electroluminescent device. The organic electroluminescent device sequentially includes a substrate, an ITO anode, a hole injection layer, a hole transport layer, a light emitting layer, a first electron transport layer, a second electron transport layer, a cathode (a magnesium-silver electrode with a Mg—Ag mass ratio of 9:1) and a cap layer (CPL), wherein the ITO anode has a thickness of 15 nm, the hole injection layer has a thickness of 10 nm, the hole transport layer has a thickness of 110 nm, the light emitting layer has a thickness of 30 nm, the first electron transport layer has a thickness of 30 nm, the second electron transport layer has a thickness of 5 nm, the magnesium-silver electrode has a thickness of 15 nm, and the cap layer has a thickness of 100 nm.

An OLED device was prepared by steps described below:

(1) A glass substrate was cut into a size of 50 mm×50 mm×0.7 mm, sonicated in isopropyl alcohol and deionized water for 30 minutes separately, and cleaned under ozone for 10 minutes. The obtained glass substrate with an ITO anode was installed onto a vacuum deposition apparatus.

(2) A thickness of 10 nm of hole injection layer material HAT-CN was deposited on the ITO anode layer by vacuum evaporation at a vacuum degree of $2\times10^{-6}$ Pa.

(3) A thickness of 110 nm of the compound M1 provided in Example 1 of the present disclosure was deposited on the hole injection layer by vacuum evaporation to serve as a hole transport layer.

(4) A thickness of 30 nm of a light emitting layer comprising CBP as a host material and Ir(ppy)$_3$ as a guest material in a mass ratio of 9:1 was co-deposited on the hole transport layer.

(5) A thickness of 30 nm of TPBi was deposited on the light emitting layer by vacuum evaporation to serve as a first electron transport layer.

(6) A thickness of 5 nm of Alq3 was deposited on the first electron transport layer by vacuum evaporation to serve as a second electron transport layer.

(7) A thickness of 15 nm of a magnesium-silver electrode was deposited on the second electron transport layer by vacuum evaporation to serve as a cathode.

(8) A thickness of 100 nm of CBP was deposited on the cathode by vacuum evaporation to serve as a cathode covering layer (a cap layer).

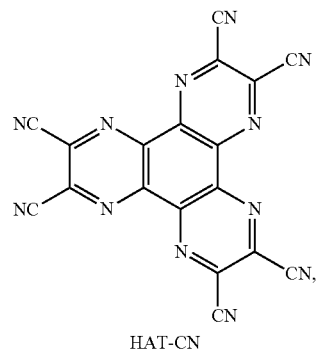

HAT-CN

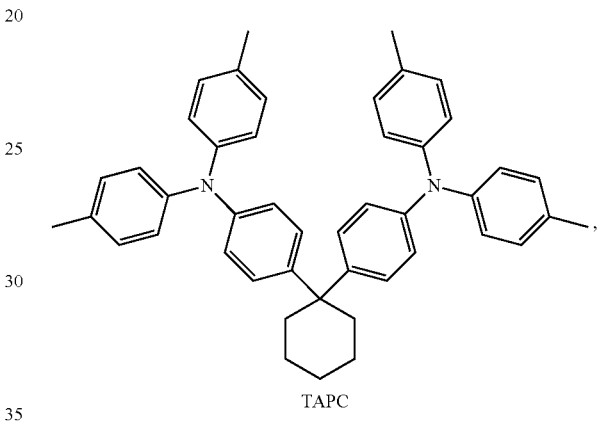

TAPC

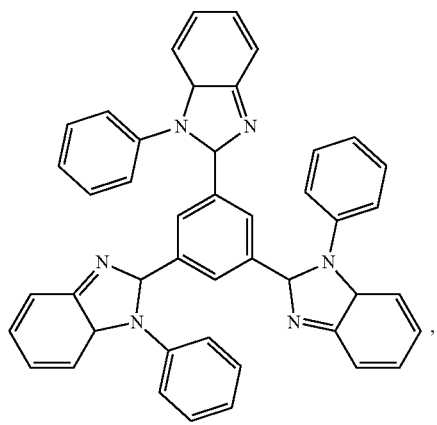

TPBi

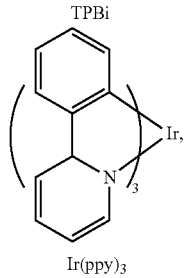

Ir(ppy)$_3$

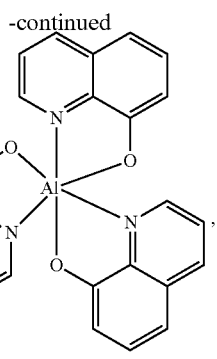

Alq3

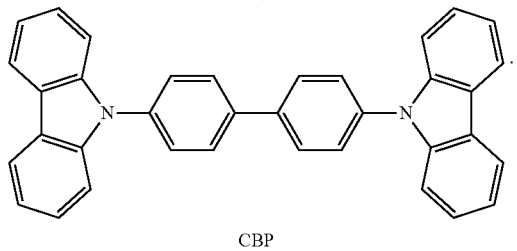

CBP

Application Example 2

This application example differs from application example 1 in that M1 in step (3) is replaced with an equivalent amount of M2.

Application Example 3

This application example differs from application example 1 in that M1 in step (3) is replaced with an equivalent amount of M43.

Application Example 4

This application example differs from application example 1 in that M1 in step (3) is replaced with an equivalent amount of M50.

Application Example 5

This application example differs from application example 1 in that M1 in step (3) is replaced with an equivalent amount of M60.

Application Example 6

This application example differs from application example 1 in that M1 in step (3) is replaced with an equivalent amount of M63.

Comparative Example 1

This application example differs from application example 1 in that M1 in step (3) is replaced with an equivalent amount of TAPC.

Comparative Example 2

This application example differs from application example 1 in that M1 in step (3) is replaced with an equivalent amount of Comparative compound 1

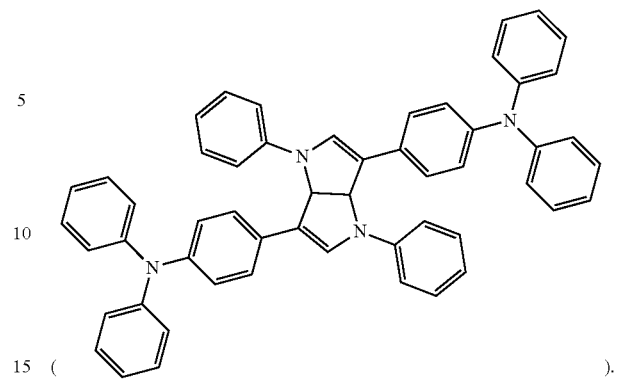

( ).

Comparative Example 3

This application example differs from application example 1 in that M1 in step (3) is replaced with an equivalent amount of Comparative compound 2

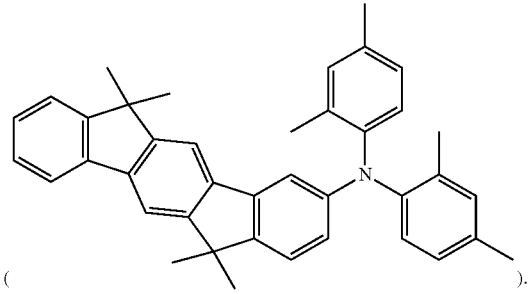 [SMILES: Cc1ccc(N(c2ccc3c(c2)-c2cc4c(cc2C3(C)C)-c2ccccc2C4(C)C)c2ccc(C)cc2C)c(C)c1]

( ).

Performance Test:
(1) Simulated Calculations of Compounds

The energy level difference between singlet and triplet states of an organic electroluminescent compound may be completed by Guassian 09 software (produced by Guassian Inc.). A specific simulation method of the energy level difference ΔEST is referred to Document J. Chem. Comput., 2013, DOI: 10.1021/ct400415r. The optimization and excitation of a molecular structure may both be completed by a TD-DFT method "B3LYP" and a basic group "6-31g (d)". Organic electroluminescent compounds M1, M2, M43, M50, M60 and M63 provided by the present disclosure were simulated according to the above-mentioned methods. Results are listed in Table 1.

TABLE 1

| Compound | HOMO (eV) | LUMO (eV) | $S_1$ (eV) | $T_1$ (eV) |
| --- | --- | --- | --- | --- |
| M1  | −5.05 | −1.92 | 3.20 | 2.77 |
| M2  | −5.03 | −1.98 | 3.21 | 2.64 |
| M43 | −5.12 | −1.99 | 3.19 | 2.63 |
| M50 | −5.10 | −1.90 | 3.11 | 2.59 |
| M60 | −5.09 | −1.89 | 3.09 | 2.71 |
| M63 | −5.06 | −1.91 | 3.07 | 2.60 |

It can be known from data in Table 1 that as a result of special design of the molecular structure, the compounds provided by the present disclosure have a deep HOMO energy level and a shallow LUMO energy level, and can effectively improve hole transport ability and block transitions of electrons; and the compounds have a high triplet energy level Ti and can effectively block transport of excitons, confine excitons in the light emitting layer, and improve transport of holes.

(2) Performance Evaluation of Organic Electroluminescent Devices

A Keithley 2365A digital nanovoltmeter was used for testing currents of the organic electroluminescent device at different voltages, and then the currents were divided by a light emitting area to obtain current densities of the organic electroluminescent device at different voltages. A Konicaminolta CS-2000 spectroradiometer was used for testing the brightness and radiant energy flux densities of the organic electroluminescent device at different voltages.

According to the current densities and brightness of the organic electroluminescent device at different voltages, current efficiency (Cd/A) and external quantum efficiency (%) at the same current density (10 mA/cm²) were obtained. A lifetime LT95 (under a testing condition of 500 nit) was obtained by measuring the time required for the brightness of an OLED device to reach 95% of its initial brightness.

The turn-on voltage ($V_{turn-on}$ in V), current efficiency (CE in Cd/A), external quantum efficiency (EQE in %) and a working lifetime ($LT_{95}$ in h) of each of organic electroluminescent devices provided in application examples 1 to 6 and comparative examples 1 to 3 were tested according to the above-mentioned method. Results are listed in Table 2.

TABLE 2

| | Hole Transport Layer | $V_{turn-on}$ (V) | CE (Cd/A) | EQE (%) | $LT_{95}$ (h) |
|---|---|---|---|---|---|
| Application example 1 | M1 | 2.98 | 9.5 | 15.8 | 113 |
| Application example 2 | M2 | 3.12 | 8.6 | 15.2 | 105 |
| Application example 3 | M43 | 2.79 | 8.5 | 14.7 | 130 |
| Application example 4 | M50 | 2.85 | 9.4 | 17.6 | 113 |
| Application example 5 | M60 | 2.74 | 8.2 | 15.9 | 106 |
| Application example 6 | M63 | 2.96 | 8.4 | 17.8 | 101 |
| Comparative example 1 | TAPC | 3.12 | 7.2 | 10.6 | 80 |
| Comparative example 2 | Comparative compound 1 | 3.26 | 5.3 | 13.2 | 60 |
| Comparative example 3 | Comparative compound 2 | 3.23 | 6.1 | 12.1 | 100 |

It can be known from data in Table 2 that compared with an organic electroluminescent device using the existing hole transport material TAPC in Comparative example 1, OLED devices provided in application examples 1 to 6 using the compounds provided by the present disclosure as the hole transport material have lower turn-on voltages (which may be as low as 2.74 V), higher current efficiency (which may reach 8.2 Cd/A to 9.5 Cd/A) and external quantum efficiency (which may reach 14.7% to 16%), and prolonged working lifetime LT95 of 101 h to 130 h. It is proved that the compound provided by the present disclosure, when used as the hole transport material of the OLED device, can improve efficiency of the device, reduce the turn-on voltage, and prolong the working lifetime.

The compound provided by the present disclosure has a parent core structure of arylpyrrole (benzopyrrole), and the compound has appropriate LUMO and HOMO energy levels, a high triplet energy level, and good mobility and solubility through the mutual coordination of the parent core structure and substituents L, $R_1$, $R_2$, $R_3$ and $R_4$, and thus improves the light emitting performance and the working lifetime of the organic electroluminescent device when used as the hole transport material. The organic electroluminescent device which uses a compound that doesn't have a parent core structure arylpyrrole (benzopyrrole) of the present disclosure (Comparative compound 1 and Comparative compound 2) as the hole transport material has a higher voltage and lower light emitting efficiency, and is difficult to meet performance requirements of high-performance light emitting devices.

The applicant has stated that although the compound, the organic electroluminescent device including the compound and the electronic apparatus of the present disclosure are described through the embodiments described above, the present disclosure is not limited to the processes and steps described above, which means that implementation of the present disclosure does not necessarily depend on the processes and steps described above. It should be apparent to those skilled in the art that any improvements made to the present disclosure, equivalent replacements of raw materials selected in the present disclosure and addition of adjuvant ingredients thereof, and selections of specific methods, etc., all fall within the protection scope and the disclosed scope of the present disclosure.

What is claimed is:

1. A compound comprising a structure represented by any one of Formula II-1 to Formula II-12:

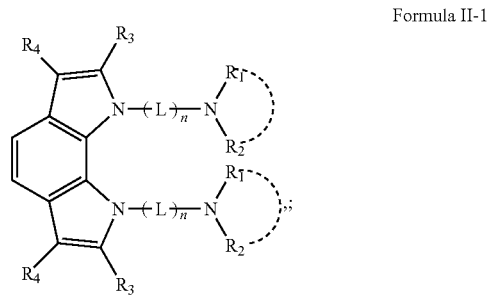

Formula II-1 wherein L is any one selected from a group consisting of substituted or unsubstituted C1 to C20 linear or branched alkylene, substituted or unsubstituted C6 to C40 arylene and substituted or unsubstituted C3 to C40 heteroarylene;

wherein $R_1$ and $R_2$ are each independently any one selected from a group consisting of substituted or unsubstituted C6 to C40 aryl and substituted or unsubstituted C3 to C40 heteroaryl, and the dashed arc between $R_1$ and $R_2$ indicates that $R_1$ and $R_2$ are not joined to each other or joined to form a ring;

wherein $R_3$ and $R_4$ are each independently any one selected from a group consisting of C1 to C20 linear or branched alkyl, C3 to C20 cycloalkyl, C6 to C30 arene and C3 to C30 heteroarene; and wherein n is 0 or 1.

2. The compound according to claim 1, wherein n is 1.

3. The compound according to claim 1, wherein L is any one selected from a group consisting of substituted or unsubstituted C6 to C20 arylene and substituted or unsubstituted C3 to C20 heteroarylene;

wherein when a substituent is present in the above groups, the substituent is at least one selected from a group consisting of C1 to C10 linear or branched alkyl, C6 to C20 aryl and cyano.

4. The compound according to claim 3, wherein L is any one selected from the following groups or any one of the following groups substituted with a substituent:

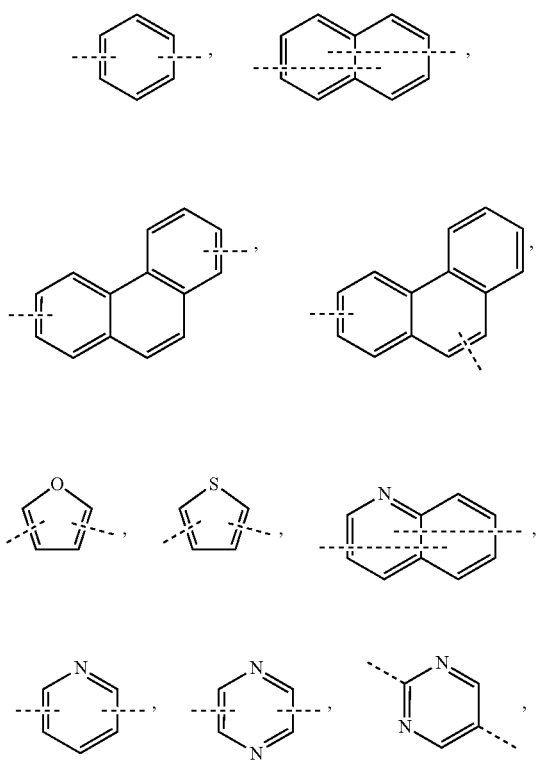

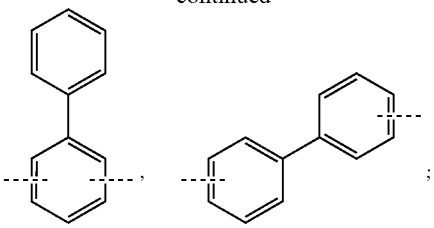

wherein the dashed line represents a linkage site of the group; and the substituent is at least one selected from a group consisting of C1 to C10 linear or branched alkyl, C6 to C20 aryl and cyano.

5. The compound according to claim 1, wherein $R_1$ and $R_2$ are each independently any one selected from a group consisting of substituted or unsubstituted C6 to C20 aryl and substituted or unsubstituted C3 to C20 heteroaryl, and $R_1$ and $R_2$ are not joined to each other or joined to form a ring;

wherein when a substituent is present in the above groups, the substituent is at least one selected from a group consisting of C1 to C10 linear or branched alkyl, C6 to C20 aryl, C3 to C15 heteroaryl and cyano.

6. The compound according to claim 1, wherein $R_1$ and $R_2$ are joined via a single bond to form a ring.

7. The compound according to claim 1, wherein $R_3$ and $R_4$ are each independently any one selected from a group consisting of C1 to C10 linear or branched alkyl, C3 to C10 cycloalkyl, C6 to C15 arene and C3 to C15 heteroarene.

* * * * *